(12) United States Patent
Yasuda et al.

(10) Patent No.: US 9,073,825 B2
(45) Date of Patent: Jul. 7, 2015

(54) METHODS AND INTERMEDIATES FOR PREPARING MACROLACTAMS

(75) Inventors: Nobuyoshi Yasuda, Mountainside, NJ (US); Jeffrey T. Kuethe, Somerset, NJ (US); Guy Humphrey, Hillsborough, NJ (US); Gregory L. Beutner, Green Brook, NJ (US); Yong-Li Zhong, Edison, NJ (US); Edward Cleator, Hoddesdon (GB); Carl Baxter, Hoddesdon (GB)

(73) Assignees: Merck Sharp & Dohme Limited, Hertfordshire (GB); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/239,391

(22) PCT Filed: Aug. 16, 2012

(86) PCT No.: PCT/US2012/051182
§ 371 (c)(1),
(2), (4) Date: Feb. 18, 2014

(87) PCT Pub. No.: WO2013/028471
PCT Pub. Date: Feb. 28, 2013

(65) Prior Publication Data
US 2014/0243519 A1 Aug. 28, 2014

Related U.S. Application Data

(60) Provisional application No. 61/539,540, filed on Sep. 27, 2011, provisional application No. 61/533,915, filed on Sep. 13, 2011, provisional application No. 61/533,439, filed on Sep. 12, 2011, provisional application No. 61/525,462, filed on Aug. 19, 2011.

(51) Int. Cl.
*A01N 43/04* (2006.01)
*A01N 43/42* (2006.01)
*C07C 35/04* (2006.01)
*C07K 5/083* (2006.01)
*C07D 403/12* (2006.01)
*C07D 498/16* (2006.01)
*C07K 5/12* (2006.01)
*C07C 67/14* (2006.01)
*C07C 69/013* (2006.01)
*C07C 69/12* (2006.01)
*C07C 269/04* (2006.01)
*C07C 271/34* (2006.01)
*A61K 38/00* (2006.01)

(52) U.S. Cl.
CPC .............. *C07C 35/04* (2013.01); *A61K 38/00* (2013.01); *C07K 5/0808* (2013.01); *C07D 403/12* (2013.01); *C07D 498/16* (2013.01); *C07K 5/126* (2013.01); *C07C 67/14* (2013.01);

*C07C 69/013* (2013.01); *C07C 69/12* (2013.01); *C07C 269/04* (2013.01); *C07C 271/34* (2013.01)

(58) Field of Classification Search
CPC .............................. A01N 43/04; A01N 43/42
USPC ................... 544/353; 560/115, 124; 568/700
See application file for complete search history.

(56) References Cited

U.S. PATENT DOCUMENTS

| 4,871,868 A | 10/1989 | Saito et al. |
| 5,715,960 A | 2/1998 | Seymour |
| 7,507,262 B2 | 3/2009 | Lim et al. |
| 2003/0186939 A1 | 10/2003 | Tani et al. |
| 2009/0155209 A1 | 6/2009 | Blatt et al. |
| 2009/0216016 A1 | 8/2009 | Yoshida et al. |
| 2009/0286778 A1 | 11/2009 | Combs et al. |
| 2010/0029666 A1 | 2/2010 | Harper et al. |

FOREIGN PATENT DOCUMENTS

| WO | WO2006102087 | 9/2006 |
| WO | WO2006119061 | 11/2006 |
| WO | WO2007015787 | 2/2007 |
| WO | WO2007015855 | 2/2007 |
| WO | WO2007016441 | 2/2007 |
| WO | WO2007131966 | 11/2007 |
| WO | WO2007148135 | 12/2007 |
| WO | WO2008051477 | 5/2008 |
| WO | WO2008051514 | 5/2008 |
| WO | WO2008057208 | 5/2008 |
| WO | WO2008057209 A1 | 5/2008 |
| WO | WO2009010804 | 1/2009 |
| WO | WO2009108507 | 9/2009 |
| WO | WO2009134624 | 11/2009 |
| WO | WO2010011566 | 1/2010 |
| WO | WO2011014487 | 2/2011 |
| WO | WO2013028465 | 2/2013 |
| WO | WO2013028470 | 2/2013 |
| WO | WO2013028471 | 2/2013 |

OTHER PUBLICATIONS

Bassan et al, Multikilogram-Scale Synthesis of a Chiral Cyclopropanol and an Investigation of the Safe Use of Lithium Acetylide-Ethylene Diamine Complex, Org. Process Res. Dev., 2012, 87-95, 16.
C. Balsano, Recent Advances in Antiviral Agents: Established and Innovative Therapies for Viral Hepatitis, Mni-Reviews in Medicinal Chemistry, 2008, pp. 307-318, 8(4).
De Francesco, Approaching a new era for hepatitis C virus therapy: inhibitors of the NS3-4A serine protease and the NS5B RNA-dependent RNA polymerase, Antiviral Research, 2003, 1-16, 58.
Gallinari et al, Modulation of Hepatitis C Virus NS3 Protease and Helicase Activities through the Interaction with NS4A, Biochemistry, 1999, 5620-5632, 38.
Gallinari et al, Multiple Enzymatic Activities Associated with Recombinant NS3 Protein of Hepatitis C Virus, J. Virol., 1998, 6758-6759, 72, No. 8.
Liverton et al, MK-7009, a Potent and Selective Inhibitor of Hepatitis C Virus NS3/4A Protease, Antimicrobial Agents and Chemotherapy, 2010, 305-311, 54, No. 1.
Liverton et al, Molecular Modeling Based Approach to Potent P2-P4 Macrocyclic Inhibitors of Hepatitis C NS3/4A Protease, J. Am. Chem. Soc., 2008, 4607-4609, 130.
Mao, A time-resolved, internally quenched fluorescence assay to characterize inhibition of hepatitis C virus nonstructural protein 3-4A protease of low enzyme concentrations, Analytical Biochemistry, 2008, 1-8, 373.

Ronn, New Developments in the Discovery of Agents to Treat Hepatitis C, Current Topics in Medicinal Chemistry, 2008, 533-562, 8.

Sarges et al, 4-Amino[1,2,4]triazolo[4,3-a]quinoxalines. A Novel Class of Potent Adenosine Receptor Antagoists and Potential Rapid-Onset Antidepressants, J. Med. Chem., 1990, 2240-2254, 33.

Sheldon, Novel protease and polymerase inhibitors for the treatment of hepatitis C virus infection, Expert Opinion Investig. Drugs, 2007, 1171-1181, 16(8).

Shirakawa et al, Preparation of (E)-1-Alkenylboronic Acid Pinacol Esters via Transfer of Alkenyl Group from Boron to Boron, Synthesis, 2004, 1814-1820, 11.

Song et al, Synthesis of Vaniprevir (MK-7009): Lactamization to Prepare a 22-Membered Macrocycle, J. Org. Chem., 2011, 7804-7815, 76.

Steven S. Carroll, Inhibition of Hepatitis C Virus RNA Replication by 2'-Modified Nucleoside Analogs, NPL-CARROLL-11979, 2003, pp. 11979-11984, 278(14).

Taliani et al, A Continuous Assay of Hepatitis C Virus Protease Based on Resonance Energy Transfer Depsipeptide Substrates, Anal. Biochem., 1996, 60-67, 240.

*Primary Examiner* — Bruck Kifle

(74) *Attorney, Agent, or Firm* — Julie M. Lake; Laura M. Ginkel

(57) ABSTRACT

A first aspect of the present invention describes a compound selected from group consisting of:

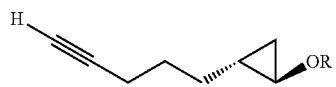

wherein R is either H, C(O)R$^A$, or C(O)NHCH(X)COOH; provided that X is a $C_2$-$C_6$ alkyl, or a $C_3$-$C_8$ cycloalkyl and R$^A$ is a $C_{1-6}$ alkyl or aryl;

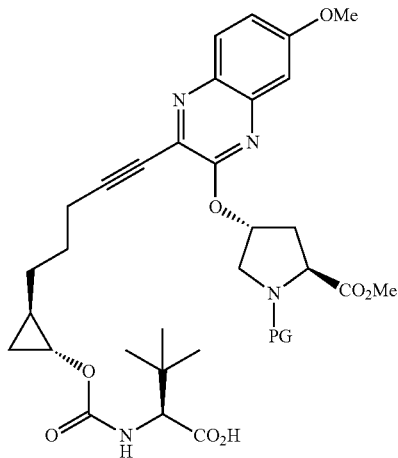

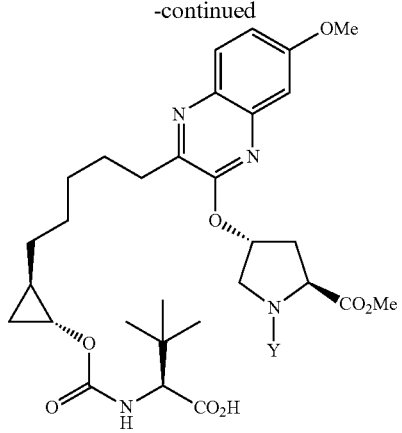

These compounds are used to make Compound A

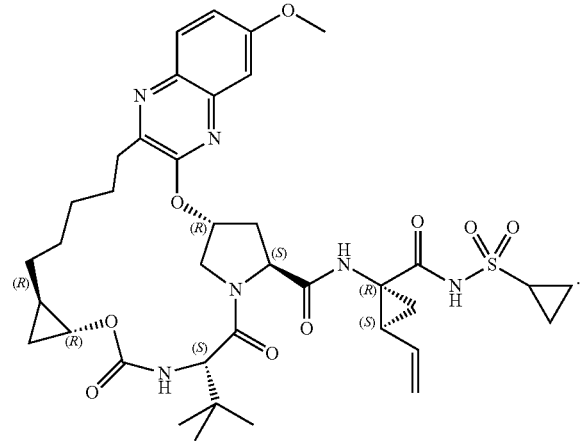

Compound A

12 Claims, 2 Drawing Sheets

METHODS AND INTERMEDIATES FOR PREPARING MACROLACTAMS

CROSS-REFERENCE TO RELATED APPLICATIONS

This application is a National Stage application of International Patent Application No. PCT/US2012/051182, filed Aug. 16, 2012, which claims the benefit of U.S. Provisional Patent Application No. 61/525,462, filed Aug. 19, 2011, U.S. Provisional Patent Application No. 61/533,439, filed Sep. 12, 2011, U.S. Provisional Patent Application No. 61/533,915, filed Sep. 13, 2011, and U.S. Provisional Patent Application No. 61/539,540, filed Sep. 27, 2011.

FIELD OF THE INVENTION

The present invention relates to process and intermediates that can be used for preparing macrolactams. One use of the methods and intermediates described herein is the production of macrolactam compounds able to inhibit HCV NS3 protease activity. HCV NS3 inhibitory compounds have therapeutic and research applications.

BACKGROUND OF THE INVENTION

Hepatitis C virus (HCV) infection is a major health problem. HCV infection leads to chronic liver disease, such as cirrhosis and hepatocellular carcinoma, in a substantial number of infected individuals.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein. NS4A provides a cofactor for NS3 activity.

Potential treatments for HCV infection are discussed in different references including Balsano, *Mini Rev. Med. Chem.* 8(4):307-318, 2008, Rönn et al., *Current Topics in Medicinal Chemistry* 8:533-562, 2008, Sheldon et al., *Expert Opin. Investig. Drugs* 16(8):1171-1181, 2007, and De Francesco et al., *Antiviral Research* 58:1-16, 2003.

Examples of publications describing macrolactam compounds able to inhibit HCV protease activity include: Harper et al., WO2010011566; Liverton et al., WO2009134624; McCauley et al., WO2009108507; Liverton et al., WO2009010804; Liverton et al., WO2008057209; Liverton et al., WO2008051477; Liverton et al., WO2008051514; Liverton et al., WO2008057208; Crescenzi et al., WO2007148135; Di Francesco et al., WO2007131966; Holloway et al., WO2007015855; Holloway et al., WO2007015787; Holloway et al., WO2007016441; Holloway et al., WO2006119061; Liverton et al., *J. Am. Chem. Soc.,* 130:4607-4609, 2008; and Liverton et al., *Antimicrobial Agents and Chemotherapy* 54:305-311, 2010.

SUMMARY OF THE INVENTION

The present invention includes methods and intermediates for preparing macrolactams. One use of the methods and intermediates described herein is in the production of macrolactam compounds able to inhibit HCV NS3 protease activity. HCV NS3 inhibitory compounds have therapeutic and research applications.

An example of a HCV inhibitory compound that can be produced using the method and intermediates described herein is Compound A, or a pharmaceutically salt thereof:

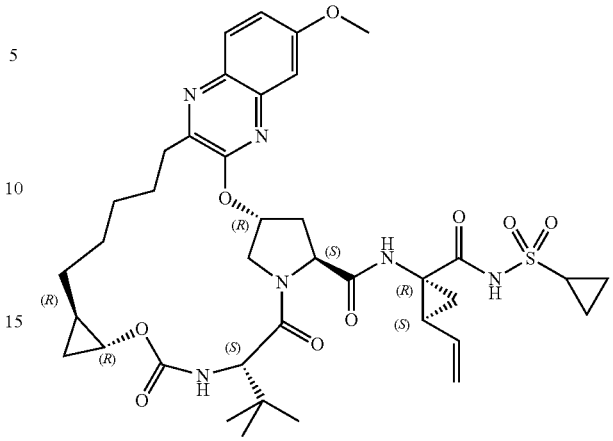

Compound A

A first aspect of the present invention describes a compound selected from group consisting of:

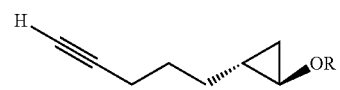

wherein R is either H, $C(O)R^4$, or $C(O)NHCH(X)COOH$; provided that X is a $C_2$-$C_6$ alkyl, or a $C_3$-$C_8$ cycloalkyl and $R^4$ is a $C_{1-6}$ alkyl or aryl,

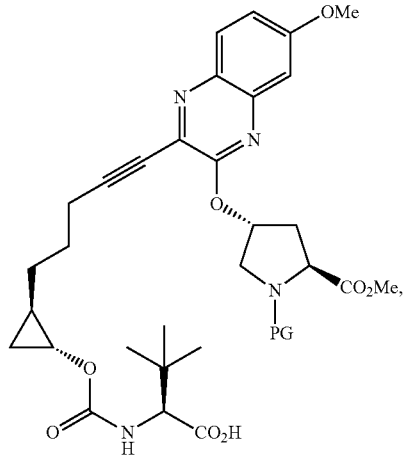

(Compound 14)

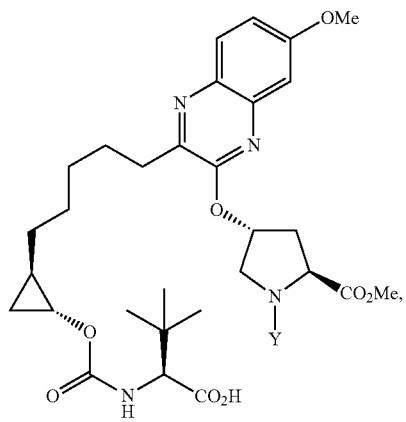

(Compound 15)

and salts thereof, wherein Y is either a protecting group or hydrogen.

Another aspect of the present invention is directed to a method of making

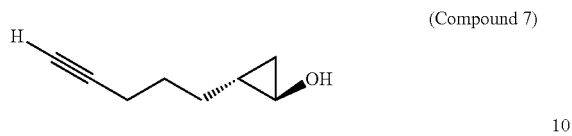
(Compound 7)

comprising the step of:

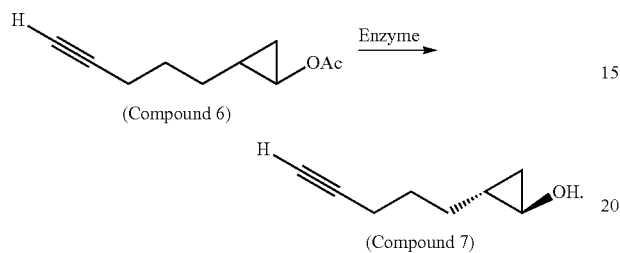

by enzymatic resolution of Compound 6. Compounds 6 are 7 are provided in a trans configuration.

Additional embodiments include methods for producing Compound 6.

Another aspect of the present invention describes a method of making a compound of:

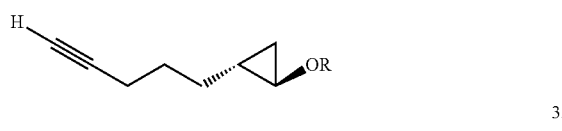

wherein R is C(O)NHCH(X)COOH, comprising the step of:

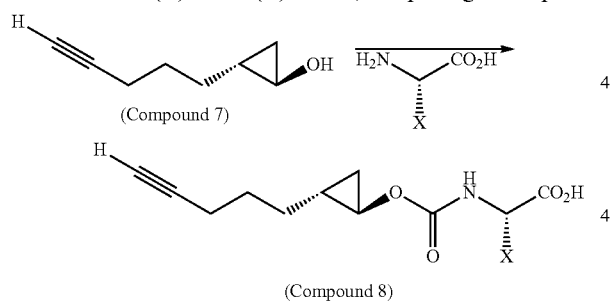

wherein X is a $C_2$-$C_6$ alkyl, or a $C_3$-$C_8$ cycloalkyl. Additional embodiments include methods of making Compound 7.

Another aspect of the present invention describes a method of producing Compound 13, comprising the step of:

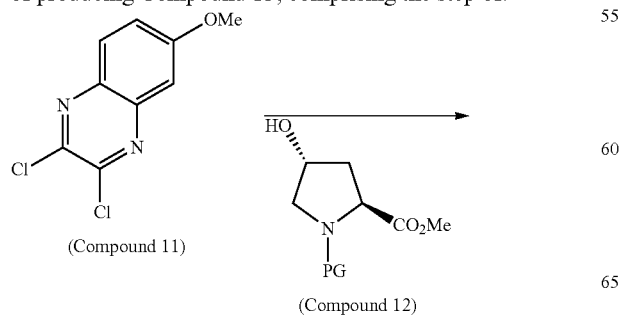

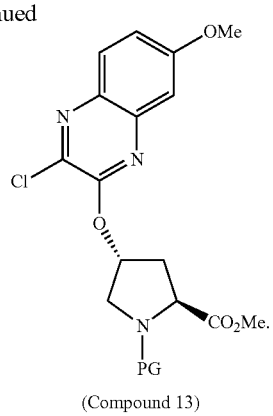
(Compound 13)

Additional embodiments include methods for producing Compound 11. "PG" refers to a protecting group.

Another aspect of the present invention describes a method for making Compound 14 comprising the step of coupling Compounds 13 and 8:

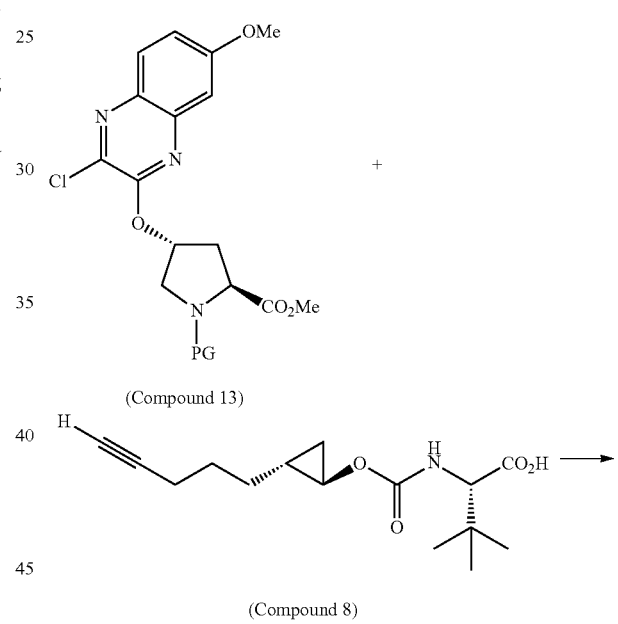

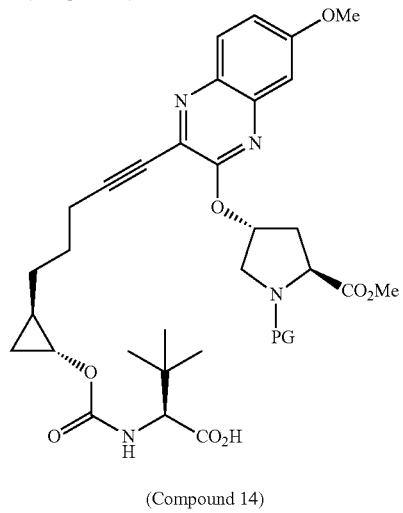
(Compound 14)

Additional embodiments include forming a macrolactam, adding functional groups; and producing Compound 13 and/or Compound 8 used in this aspect, by using methods described herein. A preferred macrolactam compound produced using methods described herein is Compound A.

Other embodiments, aspects and features of the present invention are either further described herein or will be apparent from the ensuing description, examples and appended claims.

DETAILED DESCRIPTION OF THE INVENTION

Figure 1:
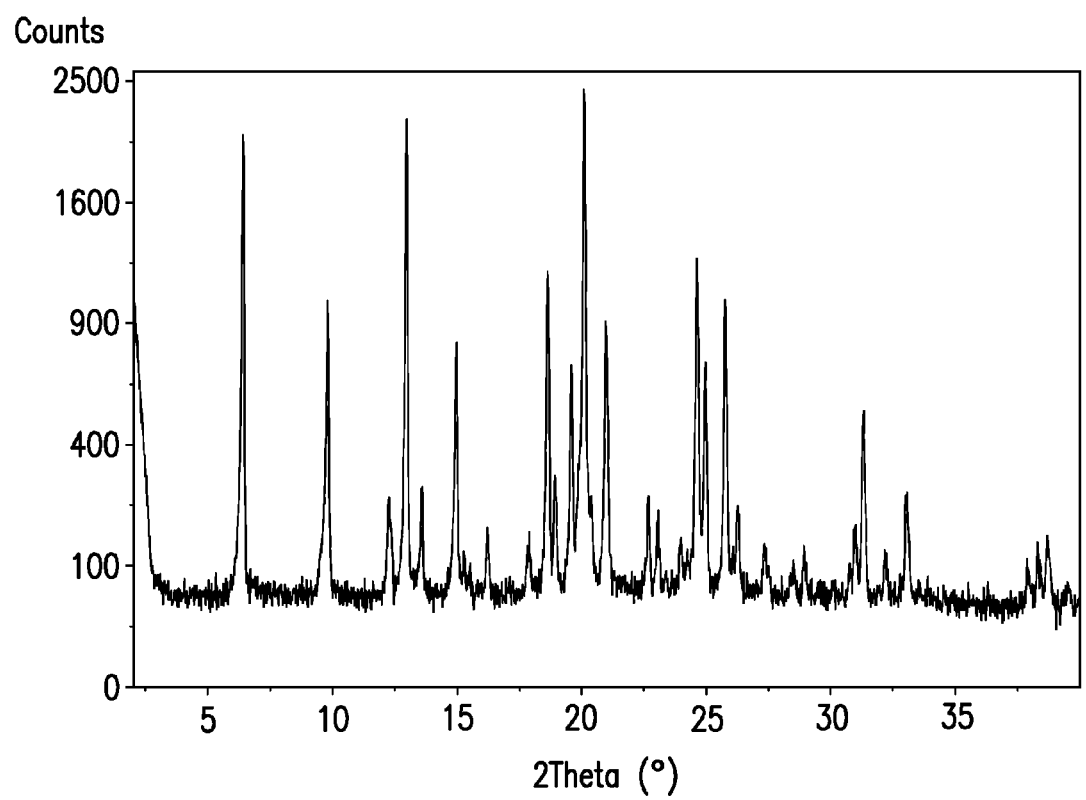
FIG. 1 illustrates an X-ray diffraction pattern of a crystalline Compound 17.

The methods and intermediates described herein can be used to synthesize macrolactams such as Compound A and compounds varying from Compound A by one or more functional group. Compound A has the following structure:

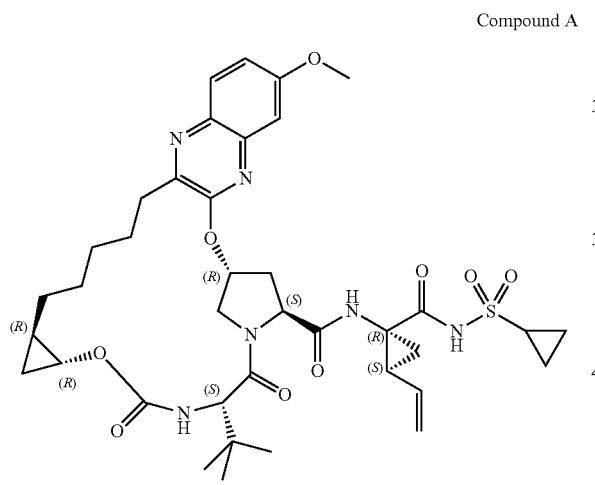

Compound A

Functional groups that can be modified include a different heterocycle group, a different alkyl in place of the t-butyl group, and alteration of the cyclopropylsulfonyl functional group (e.g., with an ethyl group replacing the ethylene and/or a methylcyclopropyl group replacing the cyclopropyl group).

Different intermediates and synthesis protocols are illustrated herein where Compound A was ultimately obtained. However, it is understood that based on the guidance provided herein other macrolactams can be produced using appropriate intermediates and by adding or modifying different functional groups. Examples of different macrolactams having different functional groups are provided in McCauley et al., WO2011014487; Harper et al., WO2010011566; Liverton et al., WO2009134624; McCauley et al., WO2009108507; Liverton et al., WO2009010804; Liverton et al., WO2008057209; Liverton et al., WO2008051477; Liverton et al., WO2008051514; Liverton et al., WO2008057208; Crescenzi et al., WO2007148135; Di Francesco et al., WO2007131966; Holloway et al., WO2007015855; Holloway et al., WO2007015787; Holloway et al., WO2007016441; Holloway et al., WO2006119061; Liverton et al., *J. Am. Chem. Soc.*, 130:4607-4609, 2008; and Liverton et al., *Antimicrobial Agents and Chemotherapy* 54:305-311, 2010.

Harper et al., WO2010011566 describes an alternative method for making Compound A. Harper et al., WO2010011566 et al., also includes data illustrating the ability of Compound A to inhibit HCV replicon activity and NS3/4A.

Intermediates and procedures that can be used to produce macrolactams can be illustrated by taking into account: (1) cyclopropyl linker synthesis: (2) heterocycle synthesis; and (3) forming a macrolactam using the cyclopropyl linker and heterocycle group, and optionally adding or modifying different functional groups. The optionally added functional groups can be used to provide for, or enhance, the ability of a compound to inhibit HCV NS3 activity and/or HCV replication.

Macrolactam compounds able to inhibit HCV activity have different uses including inhibiting HCV activity in vivo, inhibiting HCV activity in vitro, and inhibiting HCV NS3 enzymatic activity. In vivo inhibition of HCV activity can be used for therapeutic applications. Inhibiting HCV activity in vitro has different applications including being used to obtain HCV resistant mutants, further characterizing the ability of a functional group to inhibit HCV replicon or enzymatic activity, and studying HCV replication or protease activity.

Cyclopropyl Linker Synthesis

Scheme A illustrates an overall scheme for producing a cyclopropyl linker and different intermediates. Individual steps in Scheme A provide for additional embodiments. Further embodiments include steps upstream and downstream from a particular step.

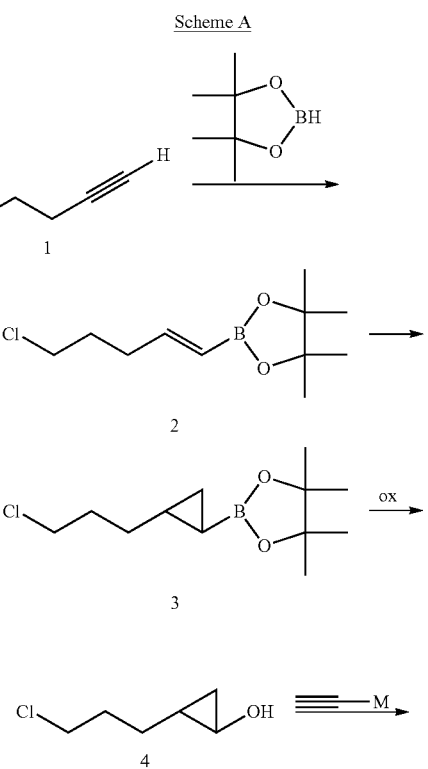

Scheme A

-continued

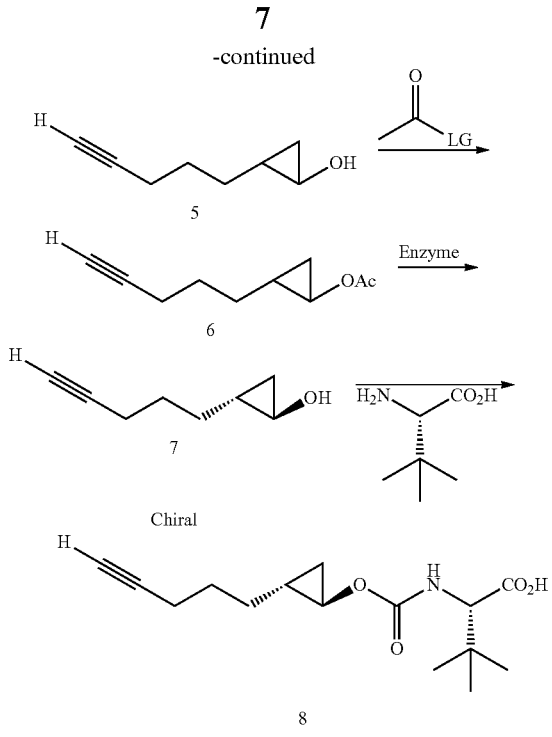

"LG" refers to leaving group.

The compounds illustrated in Scheme A are in the neutral form. It should be understood that different embodiment described throughout the application include appropriate acid or base forms of the different compounds.

Advantages of performing the different steps illustrated in Scheme A, compared with a method of producing an alternative cyclopropyl linker having an ethylene group, described in Harper et al., WO 2010/011566, include: acetylide addition to the alkyl chloride having cyclopropane function to avoid forming double cyclopropanation, selective production of chiral intermediate (Compound 7), direct carbamate formation (which does not require protection), very high trans selectivity, avoiding the use of unstable enol silyl ether, and improved yield.

Important compounds illustrated in Scheme A include Compound 7 and Compound 8. Compound 8 can be used, for example, as illustrated in Scheme C infra., to produce a macrolactam.

An aspect of the present invention is directed to a compound of Formula I:

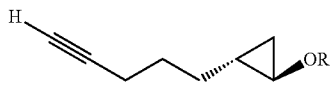

or salt thereof;
wherein R is either H, C(O)R$^A$, or C(O)NHCH(X)COOH; provided that X is a C$_2$-C$_6$ alkyl, or a C$_3$-C$_8$ cycloalkyl and R$^A$ is a C$_{1-6}$ alkyl or aryl. Variations in the X group can be used to provide modifications to Compound A.

In a first series of embodiments, R is H; R is acetyl; R is C(O)NHCH(X)COOH and X is t-butyl; R is C(O)NHCH(X)COOH and X is cyclohexyl; or R is C(O)NHCH(X)COOH and X is cyclopentyl.

In another series of embodiments, a compound of Formula I is present in a composition or mixture substantially free of its stereoisomers. Preferably, the percent of the ee form of Formula I present, with respect to other stereoisomers, is at least 90% ee, at least 95% ee, at least 90% to about 98% ee, or at least 95% to about 98% ee. In other embodiments R is H and the ee form of the compound, with respect to other stereoisomers, is at least 90% ee, at least 95% ee, at least 90% to about 98% ee, or at least 95% to about 98% ee; R is C(O)NHCH(X)COOH and the ee form of the compound, with respect to other stereoisomers, is at least 90% ee, at least 95% ee, at least 90% to about 98% ee, or at least 95% to about 98% ee; and R is C(O)NHCH(X)COOH and X is either t-butyl, cyclopentyl or cyclohexyl, preferably t-butyl, and the ee form of the compound, with respect to other stereoisomers, is at least 90% ee, at least 95% ee, at least 90% to about 98% ee, or at least 95% to about 98% ee.

Another aspect is directed to a method of producing a Formula I compound involving the enzymatic resolution of Compound 6 to produce Compound 7:

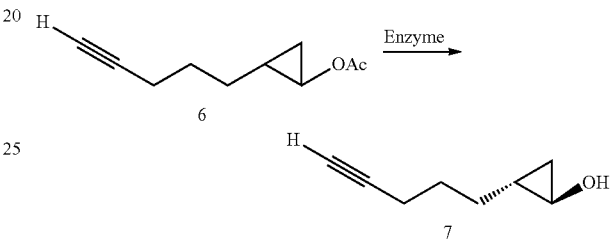

Suitable enzymes are lipases or proteases, examples of which include *Candida cylindraceae* lipase 2, *Pseudomonas cepacia* lipase 2, *Mucor miehei* lipase, papain, Amano protease S (*Bacillus stearothermophilus* protease), Amano protease A (*Aspergillus niger*), Protomax Novo, Enzyme Development Corp protese S20059, and Novozymes 435 (immobilized *Candida antarctica* lipase B). The protease from *Bacillus stearothermophilus* and Novozymes 435 are preferred, and Novozymes 435 is most preferred. The particular reaction conditions will vary depending upon the selected enzyme. In an embodiment, the enzyme is Novozyme 435 added to a buffer saturated organic solvent solution of Compound 6 at a temperature between 0 and 50° C. Preferred reaction conditions are when the solvent is MTBE saturated with a 0.1 M K$_2$HPO$_4$ solution and the reaction temperature is 10° C. Preferably, after the reaction is complete, the MTBE is removed by distillation and the resulting mixture of desired alcohol and undesired ester separated on a chromatography system.

In an embodiment Compound 7 is used to produce a Formula I compound wherein R is C(O)NHCH(X)COOH; and X either C$_2$-C$_6$ alkyl or C$_3$-C$_8$ cycloalkyl:

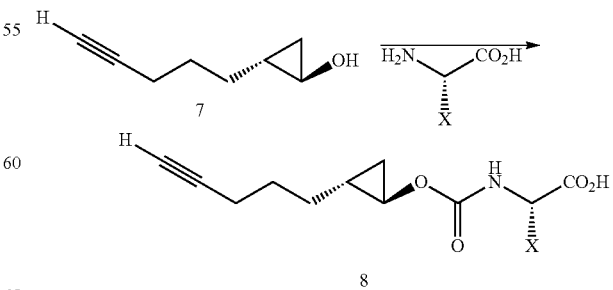

Preferably, X is either t-butyl, cyclopentyl or cyclohexyl.

The reaction can be carried using a condensation reagent, optionally in the presence of base. Examples of condensation reagents including CDI, phosgene, diphosgene, triphogene, and chlorocarbonates. CDI is a preferred reagent. In an embodiment, the reaction is carried out in the presence of base. Examples of suitable bases include typical bases and organic bases such as TEA, DIPEA, DABCO, and DBU. TEA and DIPEA are preferred reagents for this reaction.

In another embodiment Compound 6 is produced from Compound 5 using an acetylating agent:

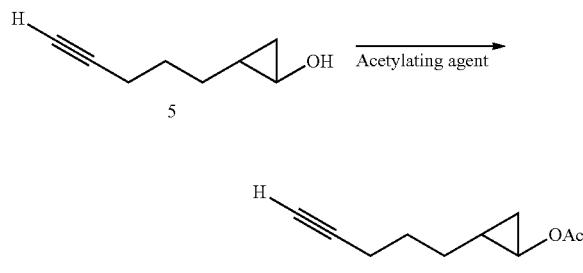

Examples of acetylating agents include acetyl chloride, acetyl bromide and acetic anhydride. Suitable reaction conditions include the use of an aprotic organic solvent at a temperature between 0 and 50° C. followed by the addition of neutral aqueous solution and separation of the organic layer to obtain Compound 6.

In another embodiment, Compound 5 is produced by mixing Compound 4 with a metal acetylide:

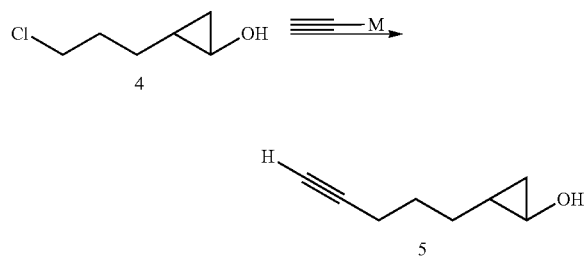

The reaction can be carried out, for example, by mixing Compound 4 in with an organometallic reagent, in an aprotic organic solvent at a temperature between −78 and 30° C. Mixing this solution with a polar aprotic solvent and a metallated acetylene at a temperature from 0-60° C. followed by addition of an acidic aqueous solution and separation of the organic layer to obtain Compound 5. Examples of organometallic reagents include alkyl lithiums, alkyl magnesium halides, sodium and potassium hydride. Examples of polar aprotic solvents include, DMSO, DMF, N,N-dimethylacetamide, N-methylpyrrolidinone, hexamethylphosphoramide and DMPU. In an embodiment, metallated acetylene, such as lithium acetylide-ethylene diamine complex or potassium acetylide is used, at a temperature from 0-60° C. followed by addition of an acidic aqueous solution and separation of the organic layer to obtain Compound 5.

In another embodiment Compound 4 is produced by oxidizing Compound 3.

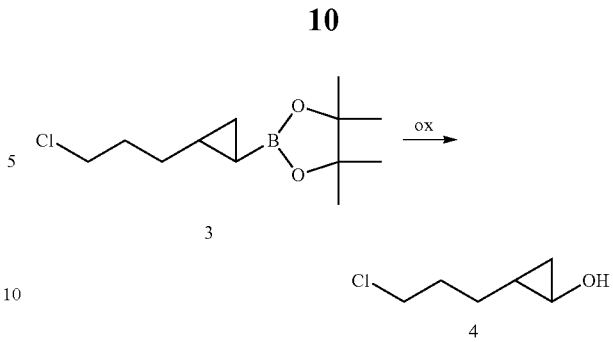

The reaction can be carried out by mixing Compound 3 with an oxidant in a protic or aprotic organic solvent at a temperature between 0 and 100° C. Examples of oxidants include hydrogen peroxide, alkyl hydrogen peroxides, sodium perborate, and sodium and potassium persulfate.

In another embodiment, Compound 3 is produced from Compound 2:

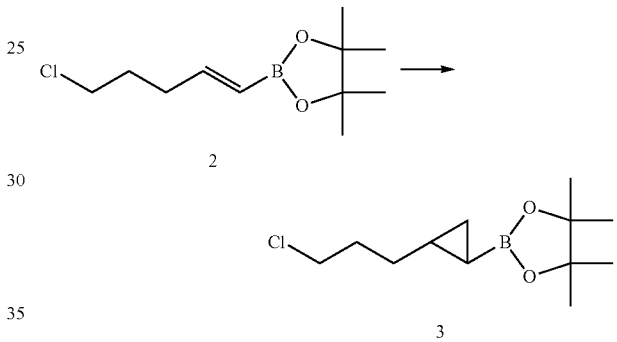

The reaction can be performed, for example, by mixing Compound 2 with an alkyl zinc reagent, an acid, and a dihalomethane in a halogenated solvent at a temperature between 0 and 40° C. followed by addition of an acidic aqueous solution and separation of the organic layer to obtain Compound 3. Examples of suitable acids include alkyl and aryl carboxylic acids, sulfonic acids or phosphoric acids.

Compound 2 can be prepared as described by Shirakawa et al. *Synthesis* 11:1814-1820, 2004.

Heterocycle Synthesis

Scheme B illustrates a scheme for producing a quinoloxine and joining it to a hydroxyproline. Individual steps in Scheme B provide for additional embodiments. Further embodiments include steps upstream and downstream from a particular step. Alternative heterocycles can be joined to hydroxyproline using the provided procedures.

Scheme B

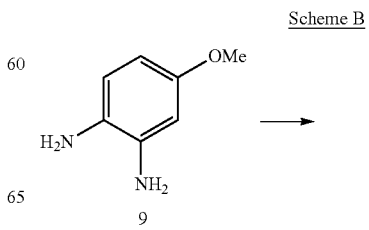

11

-continued

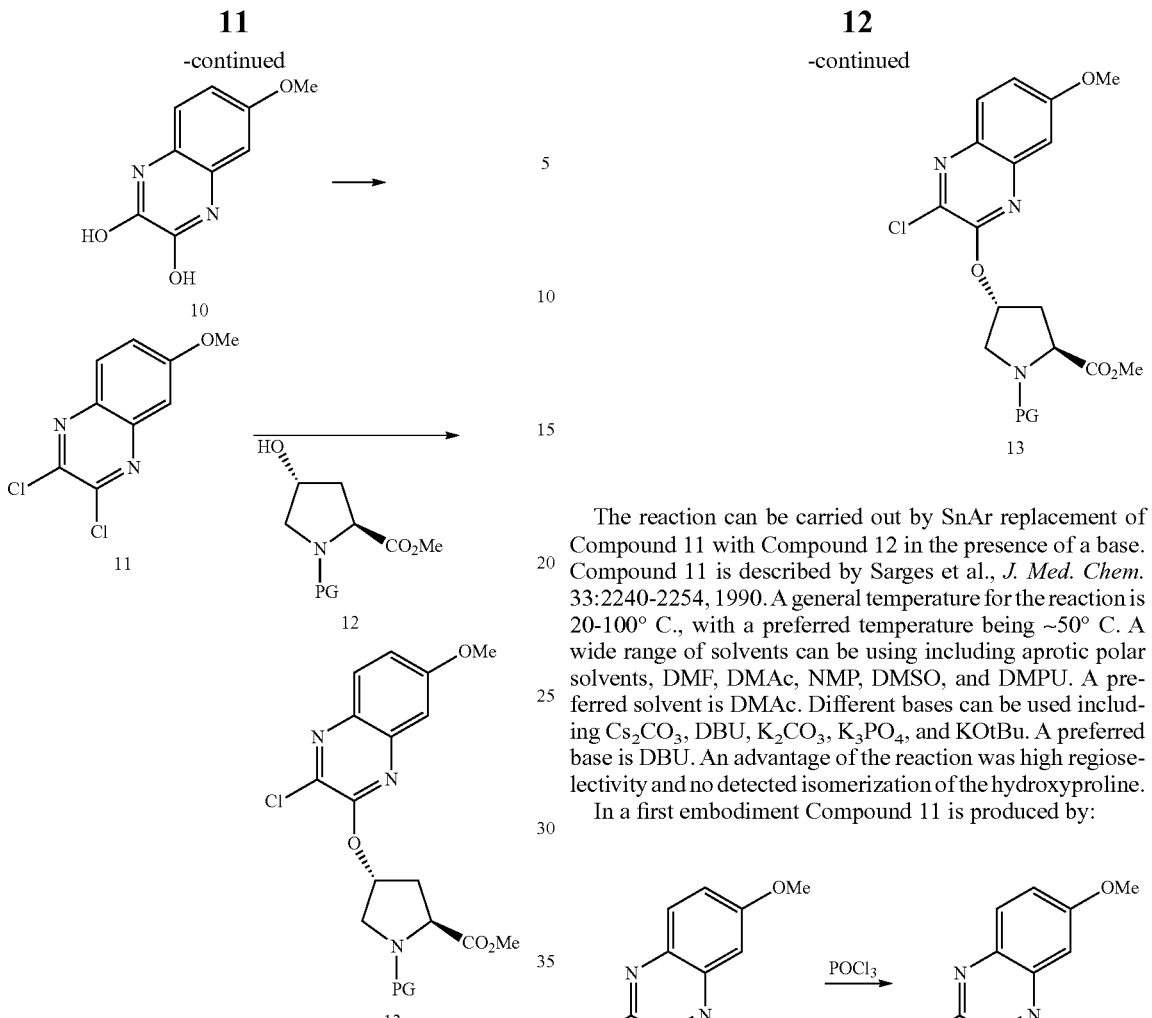

The compounds illustrated in Scheme B are in the neutral form. It should be understood that different embodiments described throughout the application include appropriate acid or base forms of the different compounds.

Advantages of the Scheme B heterocycle production and joining to hydroxylproline, compared to an alternative method described in Harper et al., WO 2010/011566 include eliminating a poor selective chloration intermediate, and eliminating four steps by allowing for the use of natural hydroxyproline.

Another aspect of the present invention is directed to production of Compound 13:

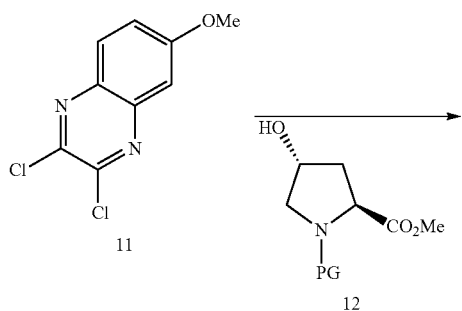

12

-continued

The reaction can be carried out by SnAr replacement of Compound 11 with Compound 12 in the presence of a base. Compound 11 is described by Sarges et al., *J. Med. Chem.* 33:2240-2254, 1990. A general temperature for the reaction is 20-100° C., with a preferred temperature being ~50° C. A wide range of solvents can be using including aprotic polar solvents, DMF, DMAc, NMP, DMSO, and DMPU. A preferred solvent is DMAc. Different bases can be used including $Cs_2CO_3$, DBU, $K_2CO_3$, $K_3PO_4$, and KOtBu. A preferred base is DBU. An advantage of the reaction was high regioselectivity and no detected isomerization of the hydroxyproline.

In a first embodiment Compound 11 is produced by:

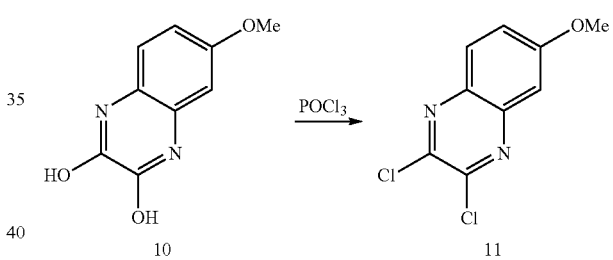

Suitable conditions are illustrated in the Examples infra.

In a second embodiment Compound 10 is produced by:

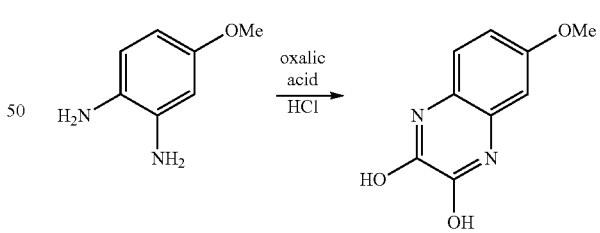

Suitable conditions are illustrated in the Examples infra.

Macrolactam Production

Macrolactam formation using a cyclopropyl linker and a heterocycle joined to hydroxyproline, followed by side chain addition is illustrated in Scheme C. Individual steps in Scheme C provide for additional embodiments. Further embodiments include steps upstream and downstream from a particular step. Important intermediate compounds illustrated in Scheme C include Compound 14, Compound 15, and Compound 16.

Alternative macrolactams can be produced based on the guidance provided herein. Potential variations include using a different linker, heterocycle, and adding different functional groups.

Scheme C

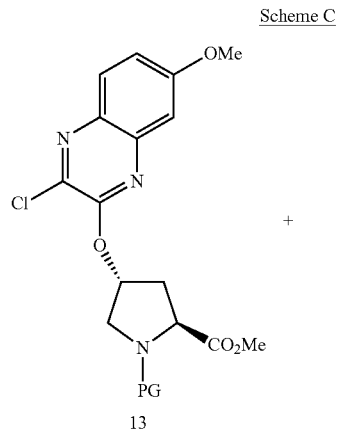

13

+

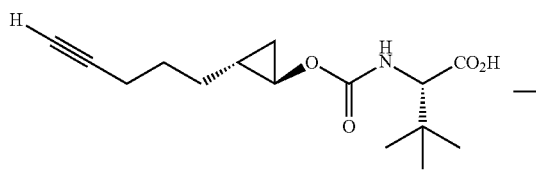

8

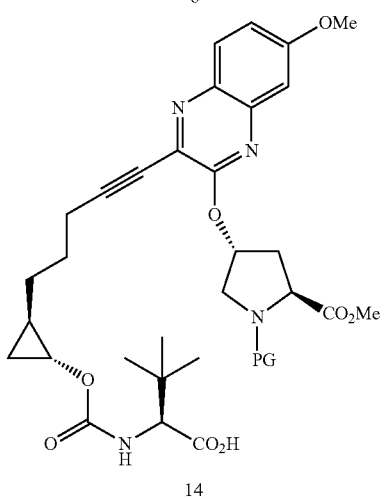

14

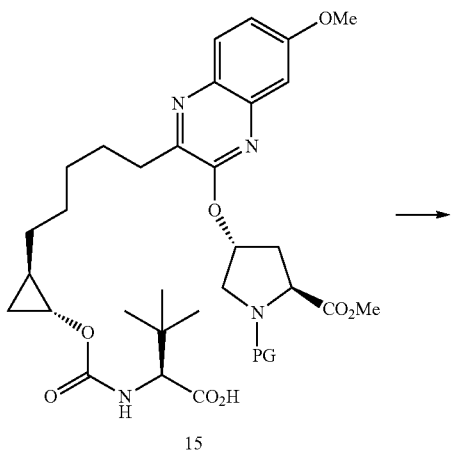

15

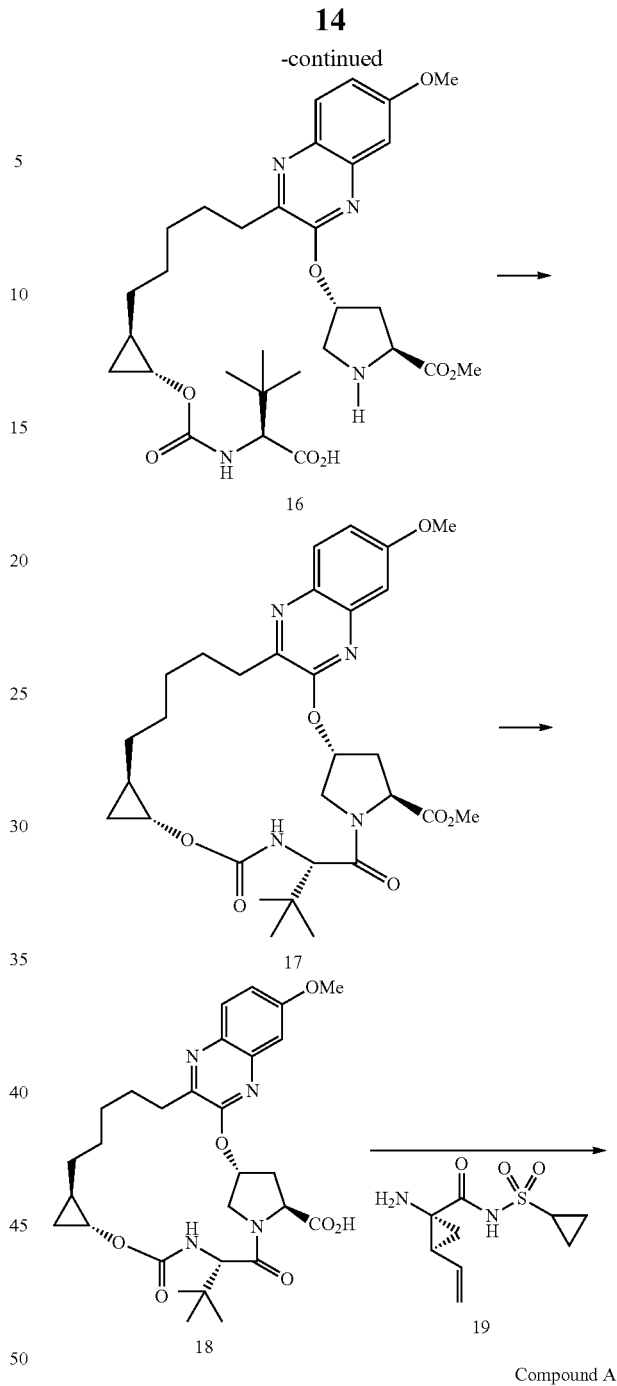

Compound A

The compounds illustrated in Scheme C are in the neutral form. It should be understood that different embodiments described throughout the application include appropriate acid or base forms of the different compounds.

Preferred reaction conditions, providing advantages compared with an alternative method described in Harper et al., WO 2010/011566 include: use of the highly effective Sonogashira/Macrolactamization method in forming Compound 14, from Compounds 8 and 13; a one-pot procedure going from Compound 14 to 15 to 16 to 17; and producing Compound A from Compounds 18 and 19 using EDC instead of HATU. Preferably, EDC coupling of Compounds 18 and 19 can be carried out using pyridine or a pyridine derivatives, where HOBt is either not present or is present in very small amounts. The use of pyridine or a pyridine derivative instead of HOBt for coupling offers several advantages including higher yield and less emerization on the proline α-center. In addition, HOBt is shock sensitive in a dry state.

An aspect of the present invention is directed to a compound selected from the group consisting of:

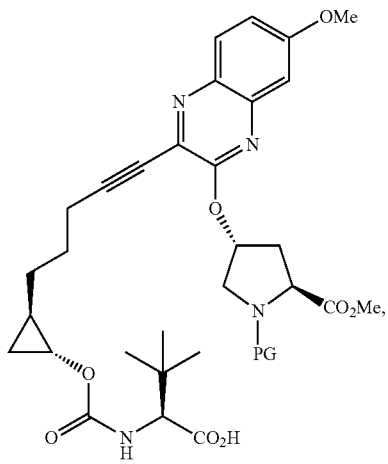

14

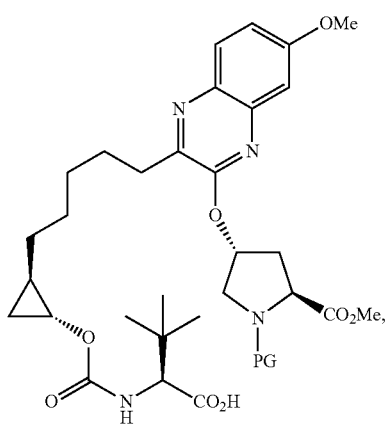

15

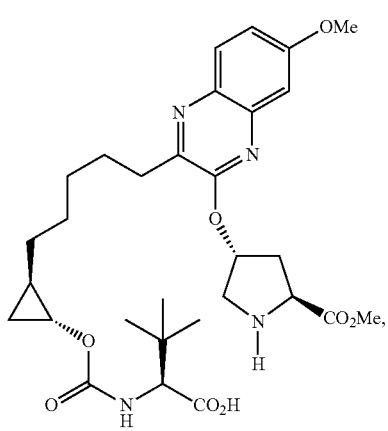

16 and salts thereof.

Another aspect of the present invention is directed to the production of Compound 14:

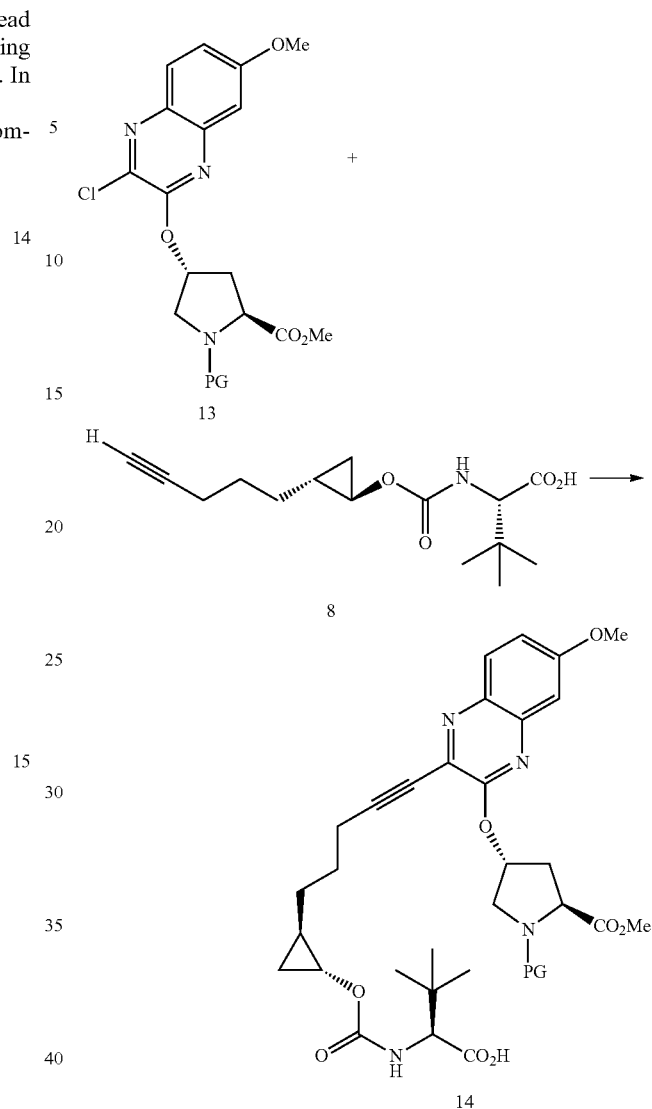

wherein any of Compounds 13, 8, and 14 (e.g., 1, 2 or all three) can be provided as salts.

A first embodiment involves Sonogashira cross coupling of Compounds 13 and 8 in the presence of tri tert-butylphosphine tetrafluoroborate salt in a solvent system. A preferred general temperature range is ~50-100° C., more preferable the temperature is about 80° C. Examples of suitable solvent systems include CPME and MeCN, THF, 2-MeTHF, toluene CPME alone and MeCN alone. A preferred solvent system is CPME and MeCN. Examples of suitable catalysts include Pd and copper. A preferred catalyst is Pd(OAc)$_2$.

In another embodiment, salts of Compound 8 are directly employed in the Sonogashira cross coupling reaction with Compound 13 to give Compound 14. This reaction can be carried out in the presence of tri tert-butylphosphine tetrafluoroborate salt in a solvent. The preferred solvent for this transformation is DMF. A preferred general temperature range is ~40-80° C., more preferable the temperature is about 65° C., and the preferred catalyst is Pd(OAc)$_2$. Examples of salt that can employed include dibenzylamine and t-butylamine.

In a second embodiment, Compound 15 is produced by hydrogenation of Compound 14:

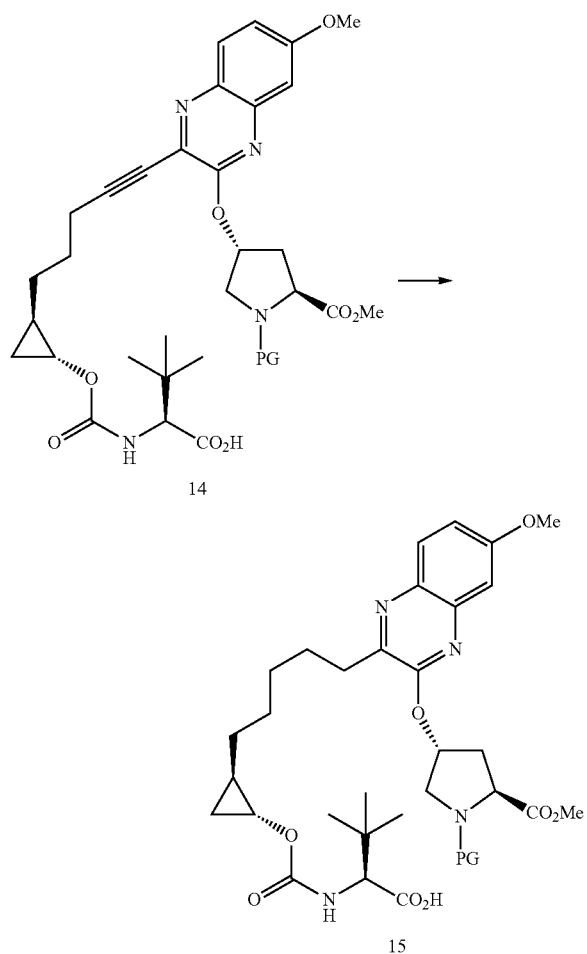

14

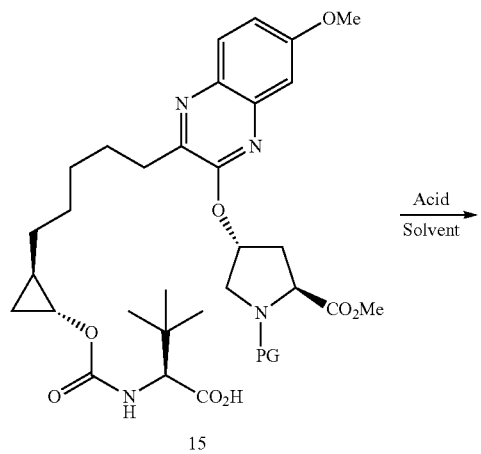

15 wherein any of Compounds 14 and 15 can be provided as salts. Suitable conditions include the use of a palladium catalyst and solvent. Examples of solvents include EtOAc, MeOH, and IPAc/MeOH mixture. IPAc/MeOH mixture is a preferred solvent. A general temperature range is 0 to 35° C., preferably 15-20° C.

In a second embodiment Compound 16 is produced:

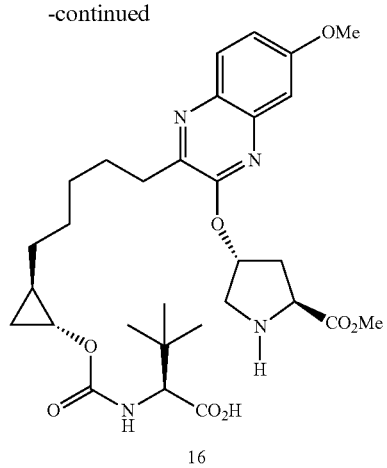

15

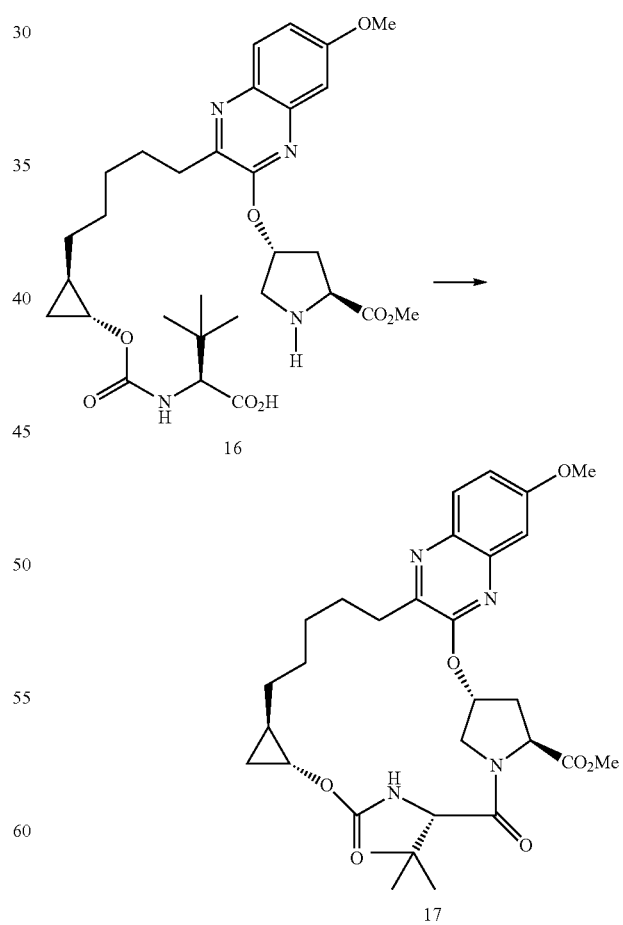

16 wherein any of Compounds 15 and 16 can be provided as salts. Suitable conditions are a range of acids and solvents. Examples of acids are methanesulfonic acid, benzenesulfonic acid, p-toluenesulfonic acid, trifluoroacetic acid, hydrochloric acid, phosphoric acid, and tetrafluoroboric acid. Examples of solvents are THF, iPrOAc, MeCN, and CH$_2$Cl$_2$.

In a third embodiment, Compound 17 is produced:

16

17 wherein any of Compounds 16 and 17 can be provided as salts. Suitable conditions are illustrated in the Examples infra.

In a sub-embodiment, the second and third embodiments are performed in a one-pot procedure for the protection/macrolactamization/isolation to provide a crystal of Compound 17.

In a fourth embodiment Compound 18 is produced:

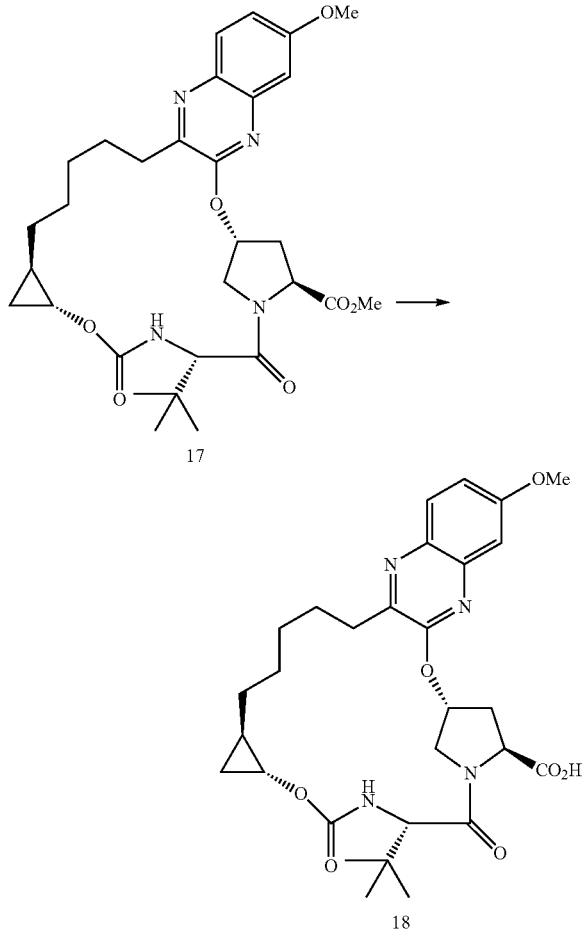

wherein any of Compounds 17 and 18 can be provided as salts. Suitable conditions are illustrated in the Examples infra.

In a fifth embodiment Compound A is produced by coupling Compound 18 with Compound 19:

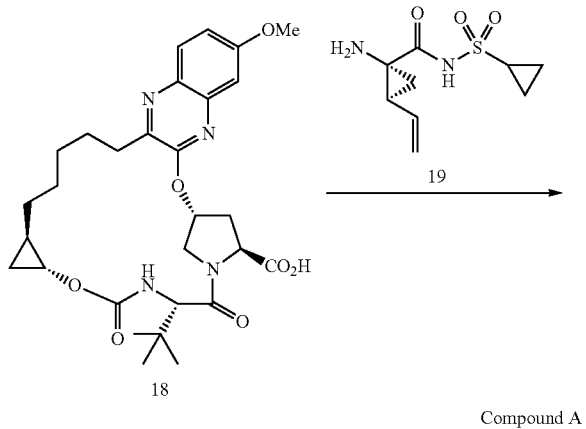

Compound A wherein any of Compounds 18, 19, or A can be provided as salts.

General coupling (condensation) reagents can be employed. The reaction can be done under standard coupling conditions with typically carbodiimide type of reagents, such as DCC, EDC, etc and in the presence or absence of HOBt, HOPO, or pyridine derivative etc. An example of suitable conditions includes using a carbodiimide, an activator and a tertiary organic base in a polar aprotic solvent at a temperature between 0 and 40° C. Examples of activators include HOBt and HOAT. In a sub-embodiment about 1.2 equiv EDC, about 2.4 equiv HOBt-H$_2$O, and about 2.4 equiv of DIPEA in about 5 volumes DMF are employed.

In another aspect, Compound A is produced by coupling Compound 18 with Compound 19 using pyridine or a pyridine derivative. Preferably, no detectable HOBt is present. The reaction can be carried out using a coupling reagent, an aprotic organic solvent and pyridine or a pyridine derivative. A general temperature is 0° C. to 50° C. (preferably room temperature). Examples of coupling reagents include dicyclohexylcarbodiimide (DCC), N,N'-diisopropylcarbodiimide (DIC), and 1-ethyl-3-(3-dimethylaminopropyl) carbodiimide (EDC). Examples of aprotic organic solvents include acetonitrile, THF, and toluene. In an embodiment EDC is used. In an embodiment, at least 10 equivalents of pyridine are used with acetonitrile.

Preferred pyridine derivatives have electron donating or neutral groups at the 3 and 4 position. Examples of general structures covering pyridine and derivatives include:

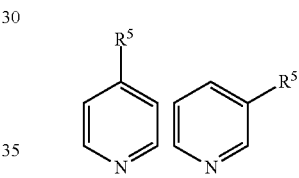

wherein $R^5$ is either hydrogen, aryl, halogen, $C_{1-6}$ alkyl, O—$C_{1-6}$ alkyl or $C_3$-$C_8$ cycloalkyl. Preferred reagents are pyridine, 4-phenylpyridine, 4-alkylpyridine, methylpyridine, 3- or 4-mono or dialkylpyridine, wherein the alkyl group can be a $C_{1-6}$ alkyl.

In additional embodiments: Compound 8 used to produce Compound 14 is produced using one or more embodiments of Scheme A, preferably all the steps in Scheme A; and/or Compound 13 used to produce Compound 14 is produced using one or more embodiments of Scheme B, preferably all the steps provided in Scheme B.

Compounds

The term "alkyl" refers to a monovalent straight or branched chain, saturated aliphatic hydrocarbon radical having a number of carbon atoms in the specified range. Thus, for example, "$C_{1-6}$ alkyl" refers to any of the hexyl alkyl and pentyl alkyl isomers as well as n-, iso-, sec- and t-butyl, n- and iso-propyl, ethyl, and methyl. As another example, "$C_{1-4}$ alkyl" refers to n-, iso-, sec- and t-butyl, n- and isopropyl, ethyl, and methyl.

The term "cycloalkyl" refers to any monocyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

Reference to "PG" indicates a protecting group. In different embodiments described throughout the application where a protecting group is employed: PG is either BOC or Fmoc; or PG is BOC.

An "aryl" is either phenyl, substituted phenyl, naphthyl, substituted naphthyl, heteroaryl, or substituted heteroaryl, provided that substituted phenyl, substituted naphthyl, and substituted heteroaryl, each have 1 to 5 substituents independently selected from the group consisting of:

(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^C)R^D$, $C(O)N(R^C)R^D$, $C(O)R^C$, $CO_2R^C$, $SR^C$, $S(O)R^C$, $SO_2R^C$, $SO_2N(R^C)R^D$, $N(R^C)C(O)R^D$, $N(R^C)CO_2R^D$, $N(R^C)SO_2R^D$, $N(R^C)SO_2N(R^C)R^D$, $OC(O)N(R^C)R^D$, $N(R^C)C(O)N(R^C)R^D$, or $N(R^C)C(O)C(O)N(R^C)R^D$,
(3) O—$C_{1-6}$ alkyl,
(4) $C_{1-6}$ halo alkyl,
(5) O—$C_{1-6}$ haloalkyl,
(6) OH,
(7) halogen,
(8) CN,
(9) $NO_2$,
(10) $N(R^C)R^D$,
(11) $C(O)N(R^C)R^D$,
(12) $C(O)R^C$,
(13) C(O)—$C_{1-6}$ haloalkyl,
(14) $C(O)OR^C$,
(15) $OC(O)N(R^C)R^D$,
(16) $SR^C$,
(17) $S(O)R^C$,
(18) $SO_2R^C$,
(19) $SO_2N(R^C)R^D$,
(20) $N(R^C)SO_2R^D$,
(21) $N(R^C)SO_2N(R^C)R^D$,
(22) $N(R^C)C(O)R^D$,
(23) $N(R^C)C(O)N(R^C)R^D$,
(24) $N(R^C)C(O)C(O)N(R^C)R^D$, or
(25) $N(R^C)CO_2R^D$; and
$R^C$ and $R^D$ are each independently H or $C_{1-6}$ alkyl.

A "heteroaryl" is a (i) a 5- or 6-membered heteroaromatic ring containing from 1 to 4 heteroatoms independently selected from N, O and S or (ii) a 9- or 10-membered bicyclic, fused ring system containing from 1 to 4 heteroatoms independently selected from N, O and S.

The atoms in a compound described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples.

Isotopically-enriched compounds described herein can be prepared without undue experimentation by conventional techniques well known to those skilled in the art or by processes analogous to those described in the Schemes and Examples provided herein using appropriate isotopically-enriched reagents and/or intermediates.

Abbreviations
BOC: t-Butyloxycarbomate
CDI: 1,1'-Carbonyldiimidazole
CPME: Cyclopentyl methyl ether
DABCO: 1,4-diazabicyclo[2.2.2.]octane
DBU: 1,8-Diazobicyclo[5.4.0]undec-7-ene
DCC: N,N'-Dicyclohexylcarbodiimide
DIC: N,N'-diisopropylcarbodiimide
DIPEA: Diisopropylethylamine
DMAc: N,N-Dimethylacetamide
DMF: N,N-Dimethylformamide
DMPU: N,N-dimethylpropyleneurea
DMSO: Dimethylsulfoxide
EDC: 1-Ethyl-3-(3-dimethylaminopropyl)carbodiimide
EtOAc: Ethyl acetate
Fmoc: 9-Fluorenylmethyloxycarbonyl
HATU: O-(7-azabenzotriazol-1-yl)-N,N,N',N'-tetramethyluronium hexafluorophoshate
HOAT: 1-Hydroxy-7-azabenzotriazole
HOBt: 1-Hydroxybenzotriazole
HOPO: 2-Hydroxypyridine-N-oxide
IPAc: Isopropyl acetate
MTBE: t-butyl methyl ether
NMP: 1N-Methylpyrrolidine
TEA: Triethylamine
THF: Tetrahydrofuran
TsOH: p-Toluenesulfonic acid Salts Compounds described herein having appropriate functional groups can be provided as salts. Examples of such compounds are described herein by reference to possible salts. Such reference is for illustration purposes, and additional embodiments include salts of the any compounds described herein having suitable groups.

Pharmaceutically acceptable salts can be used with compounds for treating patients. Non-pharmaceutical salts may, however, be useful in the preparation of intermediate compounds.

Pharmaceutically acceptable salts are suitable for administration to a patient, preferably, a human. Suitable salts include acid addition salts which may, for example, be formed by mixing a solution of a compound with a solution of a pharmaceutically acceptable acid such as hydrochloric acid, sulfuric acid, acetic acid, trifluoroacetic acid, or benzoic acid. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Administration and Compositions

Compounds described herein having therapeutic applications, such as Compound A, can be administered to a patient infected with HCV. The term "administration" and variants thereof (e.g., "administering" a compound) means providing the compound to the individual in need of treatment. When a compound is provided in combination with one or more other active agents (e.g., antiviral agents useful for treating HCV infection), "administration" and its variants are each understood to include concurrent and sequential provision of the compound or salt and other agents.

As used herein, the term "composition" is intended to encompass a product comprising the specified ingredients, as well as any product which results, directly or indirectly, from combining the specified ingredients.

By "pharmaceutically acceptable" is meant the ingredients of the pharmaceutical composition must be compatible with each other and are suitable to the recipient thereof.

The term "subject" (alternatively referred to herein as "patient") as used herein refers to an animal, preferably a mammal, most preferably a human, who is the object of treatment, observation or experiment.

The term "effective amount" indicates a sufficient amount to exert a therapeutic or prophylactic effect. For a patient infected with HCV, an effective amount is sufficient to achieve one or more of the following effects: reduce the ability of HCV to replicate, reduce HCV load, and increase viral clearance. For a patient not infected with HCV, an effective amount is sufficient to achieve one or more of the following: a reduced susceptibility to HCV infection, and a reduced ability of the infecting virus to establish persistent infection for chronic disease.

For the purpose of inhibiting HCV NS3 protease and treating HCV infection and/or reducing the likelihood or severity of symptoms of HCV infection, the compounds, optionally in the form of a salt, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice.

Compounds can, for example, be administered by one or more of the following routes: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and pharmaceutically-acceptable carriers (e.g., a carrier suitable for administration to a human patient), adjuvants and vehicles. Liquid preparations suitable for oral administration (e.g., suspensions, syrups, elixirs and the like) can be prepared according to techniques known in the art and can employ media such as water, glycols, oils, alcohols and the like. Solid preparations suitable for oral administration (e.g., powders, pills, capsules and tablets) can be prepared according to techniques known in the art and can employ solid excipients as such starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further guidance for methods suitable for use in preparing pharmaceutical compositions is provided in *Remington: The Science and Practice of Pharmacy*, 21$^{th}$ edition (Lippincott Williams & Wilkins, 2006).

Therapeutic compounds can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

HCV Inhibitory Activity

The ability of a compound to inhibit HCV NS3 activity, HCV replicon activity, and HCV replication activity can be evaluated using techniques well-known in the art. (See, for example, Carroll et al., *J. Biol. Chem.* 278:11979-11984, 2003.)

One such assay is a HCV NS3 protease time-resolved fluorescence (TRF) assay as described below and in Mao et al., *Anal. Biochem.* 373:1-8, 2008 and Mao et al., WO 2006/102087. A NS3 protease assay can be performed, for example, in a final volume of 100 µl assay buffer containing 50 mM HEPES, pH 7.5, 150 mM NaCl, 15% glycerol, 0.15% TRITON X-100, 10 mM DTT, and 0.1% PEG 8000. NS3 and NS4A are pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 µl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 µs delay. Testing concentrations of different enzyme forms are selected to result in a signal to background ratio (S/B) of 10-30. IC$_{50}$ values are derived using a standard four-parameter fit to the data. K$_i$ values are derived from IC$_{50}$ values using the following formula, $$IC_{50}=K_i(1+[S]/K_M),\qquad\qquad\text{Eqn (1)},$$

where [S] is the concentration of substrate peptide in the reaction and K$_M$ is the Michaelis constant. See P. Gallinari et al., 38 BIOCHEM. 5620-32 (1999); P. Gallinari et al., 72 J. VIROL. 6758-69 (1998); M. Taliani et al., 240 ANAL. BIOCHEM. 60-67 (1996); and Mao et al., *Analytical Biochemistry* 373: 1-8, (2008).

EXAMPLES

The examples provided below are intended to illustrate the invention and its practice. Unless otherwise provided in the claims, the examples are not to be construed as limitations on the scope or spirit of the invention.

Preparation of 2-[2-(3-Chloro-propyl)-cyclopropyl]-4,4,5,5-tetramethyl-[1,3,2]dioxaborolane (Compound 3)

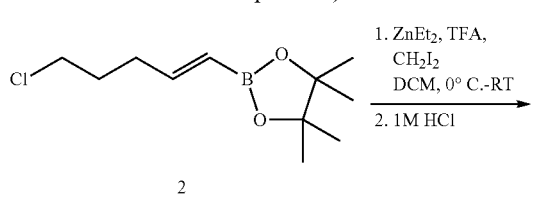

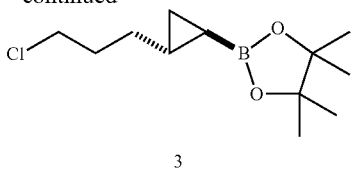

3

To a 5 L round bottomed flask equipped with a nitrogen inlet, mechanical stirrer, dropping funnel and thermocouple under N₂ was added 800 mL dichloromethane and 800 mL of a 1M diethylzinc solution in heptane (0.8 mol, 1.07 equiv). The solution was cooled with an ice bath to an internal temperature of 3° C. To the flask was then added from the dropping funnel a solution of 57.6 mL trifluoroacetic acid (0.748 mol, 1.0 equiv) in 200 mL dichloromethane over 1 hour, keeping the internal temperature below 10° C. The resulting suspension was stirred for 30 min at 3° C. To the flask was then added 72.4 mL diiodomethane (0.897 mol, 1.2 equiv) in a single portion. After stirring at 3° C. for 30 min, 172 mL of 2 (0.748 mol, 1.0 equiv) was added to the solution in a single portion. The flask was then allowed to warm to room temperature and a white precipitate began to form. After 3 hours, GC analysis indicated the reaction was at 90% conversion. The suspension was aged for an additional 17 hour or until complete consumption of 2 is observed. At that point, 800 mL of 1M HCl (0.8 mol, 1.07 equiv) was added and a +5° C. exotherm was observed. The biphasic mixture was stirred for 30 min to dissolve the precipitated solids and the organic layer was separated. Extraction of the aqueous layer with 200 mL dichloromethane, washing of the combined organic layers with 500 mL brine and concentration in vacuo gave 194 g of 3 as a yellow oil (74 wt % in DCM, 79% yield). ¹H NMR (400 MHz, CDCl₃) δ 3.59 (t, 2H, J=6.7 Hz), 1.90 (pent, 2H, J=7.1 Hz), 1.49 (sext, 1H, J=7.0 Hz), 1.36 (sext, 1H, J=7.0 Hz), 1.23 (s, 12H), 0.93 (m, 1H), 0.71 (m, 1H), 0.44 (m, 1H), −0.35 (dt, 1H, J=9.4, 5.7 Hz); ¹³C NMR (100 MHz, CDCl₃) δ 82.82, 44.74, 32.67, 32.22, 24.64, 17.22, 11.24, 0.5 (bs); GC: HP1 (30 m×0.32 mm; 0.25 μm), 25 psi, 200° C. front inlet. 5 min @ 50° C., ramp 25° C./min to 250° C. then hold for 4 min, t_r(2)=9.78 min, t_r(3)=10.08 min.

Preparation of 2-(3-Chloro-propyl)-cyclopropanol (Compound 4)

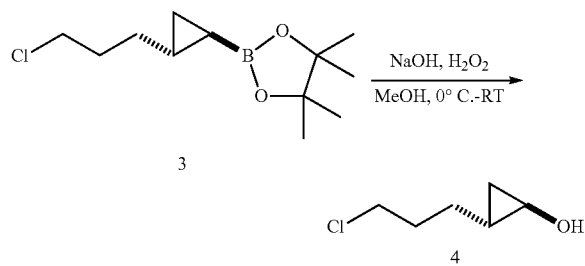

To a 3 L round bottomed flask equipped with a nitrogen inlet, mechanical stirrer, dropping funnel and thermocouple was added 143 g of 3 (0.585 mol, 1.0 equiv) in 1 L methanol. The solution was cooled with an acetone/water/dry-ice bath to an internal temperature of −8° C. To the flask was then added from the dropping funnel 58.5 mL of 10M sodium hydroxide (0.585 mol, 1.0 equiv) over 30 min, keeping the internal temperature below 10° C. After stirring for 30 min, 120 mL of 30 wt % hydrogen peroxide solution (1.17 mol, 2 equiv) was slowly added from the dropping funnel over 1 h, keeping the internal temperature below 10° C. Upon completion of the addition, the cooling bath was removed and the resulting colorless slurry was stirred at RT (room temperature) for 30 min or until complete consumption of 3 is observed by GC. The suspension was then cooled in an ice bath to an internal temperature 2° C. and 375 mL 2 M HCl is added from the dropping funnel over 30 min, keeping the internal temperature below 10° C. To this clear yellow solution at 4° C. is then slowly added 500 mL of a 1 M solution of Na₂SO₃ from the dropping funnel, keeping the internal temperature below 10° C. The resulting suspension is then filtered and extracted 3×200 mL MTBE. Concentration followed by silica gel column chromatography (6:4 hexane:ethyl acetate), to remove pinacol, gave 60.6 g of product 4 as a clear oil (90 wt %, 69% yield). ¹H NMR (400 MHz, CDCl₃) δ 3.62 (t, 2H, J=6.6 Hz), 3.27 (dt, 1H, J=6.3, 2.6 Hz), 1.89 (pent, 2H, J=6.8 Hz), 1.85 (bs, OH), 1.43 (sext, 1H, J=7.0 Hz), 1.28 (sext, 1H, J=7.0 Hz), 0.94 (m, 1H), 0.75 (m, 1H), 0.38 (q, 1H, J=6.0 Hz); ¹³C NMR (100 MHz, CDCl₃) δ 52.21, 44.69, 31.91, 28.69, 19.69, 14.15; GC: HP1 (30 m×0.32 mm; 0.25 μm), 25 psi, 200° C. front inlet. 5 min @ 50° C., ramp 25° C./min to 250° C. then hold for 4 min, t_r(3)=10.08 min, t_r(4)=7.15 min.

Preparation of 2-Pent-4-ynyl-cyclopropanol (rac-Compound 5)

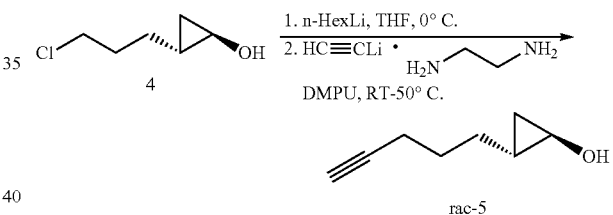

To a 2-neck 15-mL round bottomed flask equipped with a temperature probe, N₂ inlet, and septum was added 1 g of 4 (7.28 mmol, 1.0 equiv) and 3.0 mL THF. The solution was cooled to an internal temperature of 0° C. with an ice bath. To this solution was added 2.95 mL of 33 wt % n-Hexyllithium (7.28 mmol, 1.0 equiv) slowly via syringe pump over 1 hour. Internal temperature rose to 6.8° C. and solution became yellow. In a separate 3-neck 100-mL round bottomed flask equipped with a temperature probe, N₂ inlet, and septum 0.82 g of lithium acetylide-ethylenediamine complex (8.01 mmol, 1.1 equiv) was slurried in 5.0 mL of DMPU at room temperature. To this room temperature slurry, the cold solution of the deprotonated cyclopropanol was transferred via cannula over 5 min. After the addition, the brown mixture was heated to an internal temperature of 52° C. with a heating mantle for 3 hours or until greater than 98% conversion was observed by GC. The brown mixture was cooled with an ice bath to 3° C. and then the ice bath was removed to prevent freezing. To this was slowly added 17.5 mL of 0.5 N HCl and an ice bath was applied to maintain an internal temperature below 21° C. The mixture was then diluted with 10 mL MTBE and 5 mL of water before transfer to a separatory funnel and removal of the aqueous layer. The aqueous layer was extracted once with 15 mL MTBE and then the combined organic layers were washed with 20 mL water followed by 20 mL brine. The organic layer was then concentrated in vacuo to afford 1.27 g of rac-5 as a yellow oil (72 wt %, 98% yield). $^1$H NMR (400 MHz, CDCl$_3$) δ 3.24 (dt, 1H, J=2.6, 5.3 Hz), 2.25 (dt, 2H, J=2.6, 7.6 Hz), 1.96 (t, 1H, J=2.6 Hz), 1.92 (s, 1H, OH), 1.64 (pent, 2H, J=7.3 Hz), 1.38 (sext, 1H, J=6.9 Hz), 1.24 (sext, 1H, J=6.9 Hz), 0.93 (m, 1H), 0.72 (m, 1H), 0.35 (q, 1H, J=6.0 Hz); $^{13}$C NMR (100 MHz, CDCl$_3$) δ 84.49, 68.37, 52.45, 30.50, 27.74, 20.17, 18.01, 14.25; GC: HP1 (30 m×0.32 mm; 0.25 μm), 25 psi, 200° C. front inlet. 5 min @ 50° C., ramp 25° C./min to 250° C. then hold for 4 min, t$_r$(4)=7.15 min, t$_r$(rac-5)=6.72 min.

Preparation of Acetic Acid racemic trans-2-pent-4-ynyl-cyclopropyl ester (rac-Compound 6)

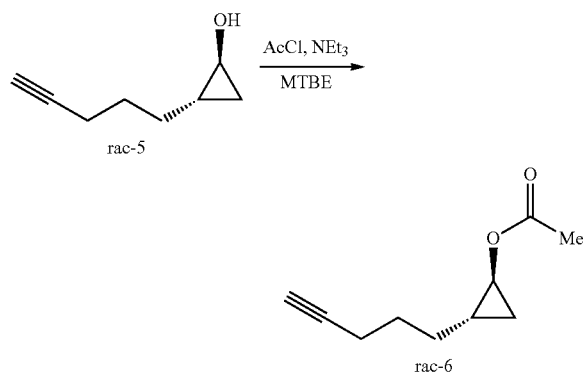

To a 5 L round bottomed flask equipped with a nitrogen inlet, mechanical stirrer, dropping funnel and thermocouple under N$_2$ was added 31.2 g of rac-5 (251 mmol, 1.0 equiv), 350 mL of MTBE and 45.5 mL of triethylamine (327 mmol, 1.3 equiv) prior to cooling the solution in an acetone/ice bath to an internal temp of <5° C. To the solution was added from the dropping funnel 23.7 mL acetyl chloride (301 mmol, 1.1 equiv) over a 30 min period while maintaining the internal temp <10° C. The resulting slurry was then warmed to room temperature and aged for 2 hours. At this point, the reaction mixture was diluted with 200 mL of water. The biphasic mixture was transferred to a separatory funnel and the aqueous layer removed. The organic layer was washed with 200 mL of 2 N HCl and then with 300 mL of sat. NaHCO$_3$ prior to drying over MgSO$_4$. The solvent was removed in vacuo to give 41.8 g of rac-6 (>99% yield). $^1$H NMR (400 MHz, CDCl$_3$) δ 3.84 (dt, 1H, J=6.7, 2.9 Hz), 2.25 (dt, 2H, J=2.7, 7.0 Hz), 2.03 (s, 3H), 1.95 (t, 1H, J=2.6 Hz), 1.67 (m, 2H), 1.39 (m, 2H), 1.01 (m, 1H), 0.89 (m, 1H), 0.57 (q, 1H, J=6.5 Hz); $^{13}$C NMR (100 MHz, CDCl$_3$) δ 171.60, 84.15, 68.47, 54.20, 30.12, 27.40, 20.85, 17.92, 17.83, 11.81; GC: Restek RT-Bdex SA (30 m×0.25 mm×0.25 μm), 60 cm/s linear velocity, 20:1 split, 120° C. isothermal, t$_r$(5)=25.0, 29.6 min, t$_r$(6)=17.1, 17.5 min.

Preparation of (1R,2R)-2-Pent-4-ynyl-cyclopropanol (ent-Compound 5)

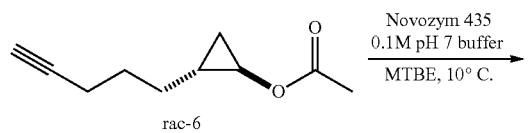

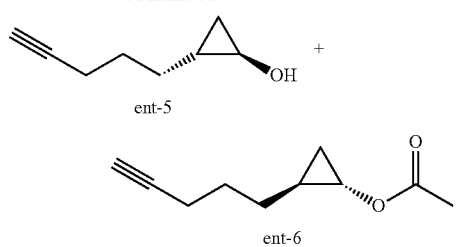

To a 1-L round bottom flask equipped with an overhead stirrer and temperature probe was added a 60 wt % solution of rac-6 in MTBE (44.8 g, 0.27 mol) and an additional 730 ml of MTBE that had been saturated with aqueous 0.1 M pH 7 phosphate buffer, giving a final solution concentration of rac-6 of 60 g/l. The flask was placed in an ice bath to maintain an internal temperature of approximately 10° C. throughout the hydrolysis reaction, which was initiated by the addition of 730 mg Novozym 435. The reaction was aged at 10° C. for approximately 4 hr until conversion had reached 41%, at which point the ee of ent-5 was 96%. The reaction mixture was then filtered through a 150-ml medium-pore glass filter funnel and the solid immobilized enzyme was washed three times with 80 ml MTBE. The resulting MTBE solution was then solvent switched to heptane. The mixture in heptane (39.2 kg, approximately 50 L) was applied to a Biotage Flash 400 L cartridge (40×60 cm, 40 kg silica gel, 60 angstrom, 40-63 um) and eluted sequentially with 165 L of 2.5:97.5, 75 L of 10:90, and 330 L of 25:75 EtOAc/heptane (v/v). After the mixture was applied to the column, 18 L fractions were taken. The rich cut fractions of the alcohol ent-5 were located by TLC (silica, 20% EtOAc/heptane) and then analyzed by GC(HP-1, 30 m×320 μm×0.25 μm film, 9.14 psi constant He pressure, 15:1 split, 50° C. for 5 min then 25 deg/min to 275° C. and hold 5 min, RT of alcohol 8.8 min). Fractions 15-21 were concentrated to give 3.48 kg (80 wt %, 92% ee, 30% yield from rac-6) of the desired ent-5.

GC: Restek RT-Bdex SA (30 m×0.25 mm×0.25 μm), 60 cm/s linear velocity, 20:1 split, 120° C. isothermal, t$_r$(5)=25.0, 29.6 min, t$_r$(6)=17.1, 17.5 min.

Preparation of (S)-3,3-dimethyl-2-(((((1R,2R)-2-(pent-4-yn-1-yl)cyclopropoxy)carbonyl)amino)butanoic acid (Compound 8)

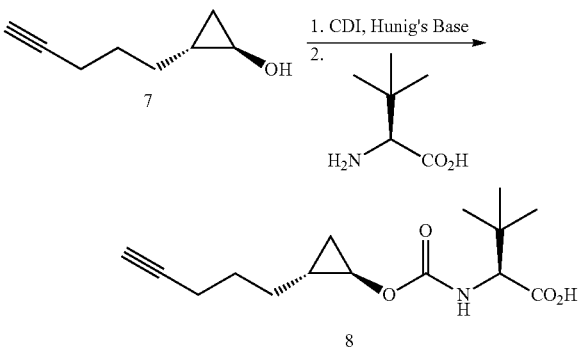

TABLE 1

| Materials | MW | Amount | Mole | Equiv |
|---|---|---|---|---|
| Cyclopropanol 7 | 124.18 | 2.816 kg | 22.68 | 1.00 |
| CDI | 162.15 | 3.86 kg | 23.81 | 1.05 |
| Hunigs base | 129.24 | 14.1 L | | |
| L-tert-leucine | 131.17 | 3.57 kg | 27.2 | 1.20 |

In a 50 L round bottom flask equipped with a mechanical stirrer, thermocouple and reflux condenser was added the starting Compound 7 (3.477 kg @ 81 wt % by NMR, 92% ee) and 14.1 L (5 L/kg) of Hunigs base. To the resulting homogeneous solution was added CDI portion wise as a solid while maintaining the internal temperature between 21-25° C. The resulting slurry was aged at room temperature for 1 hour. To the slurry was added L-tert-leucine as a solid and the reaction mixture was heated to an internal temperature of 95° C. for 2.5 hours. The reaction mixture was cooled to room temperature with the aid of an ice-bath and diluted with 17 L of water. The mixture was aged for 30 min to dissolve all the solids and then transferred to a 100 L cylindrical extractor. The aqueous layer was then washed with 12 L of MTBE. The bottom aqueous layer was drained and the top MTBE layer was discarded. The aqueous layer was washed with 8 L of MTBE. The bottom aqueous layer was drained and the top MTBE layer was discarded.

The resulting aqueous layer was added back into the 100 L extractor and made acidic with concentrated HCl to a final pH of 1.5-2.0. The biphasic mixture was extracted with MTBE (2×12 L) and the extracts were washed with 6 L of water and then 5 L of brine. NMR assay yield of the product Compound 8 at this point gave 4.49 kg (70.4%, 20.7 kg wt of solution, 21.7 wt % product).

The MTBE layer was then transferred via vacuum into a 50 L round bottom flask equipped with a mechanical stirrer, thermocouple, and batch concentrator and the solvent was removed under reduced pressure keeping the internal temperature of the batch <20° C. during the distillation. The solvent was then switched to cyclopentyl methyl ether (CPME) by flushing with ~5 L of CPME and then diluted to a final volume of ~20 L. This material was used in the next reaction without further purification.

An analytical sample was obtained by silica gel chromatography as a colorless oil: $^1$H NMR (CDCl$_3$, 400 MHz) δ 0.54 (q, 1H, J=6.4 Hz), 0.83 (m, 1H), 0.99 (m, 1H), 1.01 (s, 9H), 1.40 (m, 2H), 1.67 (m, 2H), 1.94 (t, 1H, J=2.6 Hz), 2.23 (m, 2H), 3.77 (br m, 1H), 4.20 (br m, 1H), 5.28 (br m, 1H), 9.40 (br s, 1H); $^{13}$C NMR (CDCl$_3$, 100 MHz) δ 11.8, 18.0, 26.5, 27.4, 30.1, 34.6, 55.0, 62.0, 68.4, 84.2, 156.7, 175.8.

Example 2

Heterocycle Production

Preparation of 6-Methoxy-quinoxaline-2,3-diol (Compound 10)

TABLE 2

| Materials | MW | Amount | Mole | Equiv |
|---|---|---|---|---|
| Diamine 9 | 211.09 | 2.597 kg | 12.30 | 1.00 |
| Oxalic acid | 90.03 | 1.55 kg | 17.22 | 1.40 |
| 3N HCl | | 17.8 L | | |

In a 50 L round bottomed flask equipped with a mechanical stirrer, thermocouple and condenser was added 4-methoxy-1,2-phenylenediamine dihydrochloride salt (Compound 9) (2.65 kg @ 98 wt %, 12.30 mol), oxalic acid (1.582 kg @ 98 wt. %, 17.22 mol) and 3N HCl$_{(aq)}$ (17.8 L) under nitrogen. The grey heterogeneous slurry was heated to 90° C. with steam for 7.25 hours. The reaction was monitored by HPLC. The resulting grey slurry was then cooled to an internal temperature of 20° C. overnight The slurry was filtered, water (1.0-1.5 L/Kg) was used to help with the transfer. The light grey solids were washed with 2 cake volumes water (5.0-5.5 L/Kg). The solids were dried under vacuum/N$_2$ sweep for 24 hours, at which time the solids were still very wet. The product was then slurry washed with methanol, and dried over 48 hours at 40-45° C. in a vacuum oven to give 2.304 kg of Compound 10 as an off-white product (97% yield) of 99.95% purity by HPLC assay. There was no methanol by NMR and the KF=0.05 wt. % water.

HPLC Conditions: Zorbax Eclipse Plus C18 50×4.6 mm, 1.8 um, 1.5 mL/min, 210 nm, 25° C., Eluents: Water 0.1% H$_3$PO$_4$ (A), Acetonitrile (B). 90% A 0 min, 5% A 5 min, 5% A 6 min

| | |
|---|---|
| Compound 9 (diamine HCl salt) | 0.394 min |
| Compound 10 | 1.55 min (sometimes two peaks) |

Preparation of 2,3-Dichloro-6-methoxyquinoxaline (Compound 11)

Chemical Formula: C$_9$H$_8$N$_2$O$_3$
Molecular Weight: 192.17

Chemical Formula: C$_9$H$_6$Cl$_2$N$_2$O
Molecular Weight: 229.06

TABLE 3

| Materials | MW | Amount | Mole | Equiv |
|---|---|---|---|---|
| Diol 10 | 192.17 | 3.80 kg | 19.77 | 1.00 |
| POCl$_3$ | 153.33 | 5.92 L | 63.5 | 3.20 |
| MeCN | | 25 L | | |

In a 22 L round bottomed flask equipped with a mechanical stirrer, thermocouple and condenser was added to Compound 10 (3.8 kg), and charged slowly at room temperature with POCl$_3$ (5.92 L @ 99%). There was no initial temperature change. The grey slurry was heated to 98° C. for 20 hours. After 2-3 hours the slurry turned from grey to green, then to yellow and finally turned homogeneous red. As the slurry became homogenous in POCl$_3$, significant amounts of HCl off-gassing were produced. The reaction was monitored by HPLC. The dark red, homogenous solution was allowed to cool slowly to below 80° C. At this point 19 L of acetonitrile (5.0 L/Kg) was charged which produced a dark brown slurry. The reaction was cooled to 10-15° C. in an ice bath and reverse quenched into 45.6 L of cold water (12.0 L/Kg) in a 100 L cylindrical vessel. This exothermic quench was kept below 27° C. MeCN (~4 L) was used to aide in slurry transfer. The brown slurry was filtered and 5 L of water was used to wash the flask. The solids were washed with 1 cake volume of water (~5 L). The pH of the filtrate was acidic. The solids were next displacement washed with 2 cake volumes of 5% sodium bicarbonate (~20.00 L). The pH was between 8-9. A slurry wash was performed with 2 cake volumes of water (20 L total). The pH did not change. The solids were dried for 72 hours under reduced pressure and nitrogen flow to give 4.464 kg of tan product Compound 11 (99% yield) of 99.5% purity by HPLC assay with KF=0.5 wt. % water.

HPLC Conditions: Zorbax Eclipse Plus C18 50×4.6 mm, 1.8 um, 1.5 mL/min, 210 nm, 25° C., Eluents: Water 0.1% H$_3$PO$_4$ (A), Acetonitrile (B). 90% A 0 min, 5% A 5 min, 5% A 6 min

| Compound 10 | 1.55 min (sometimes two peaks) |
|---|---|
| Compound 11 | 4.55 min |

Preparation of Ether (Compound 13)

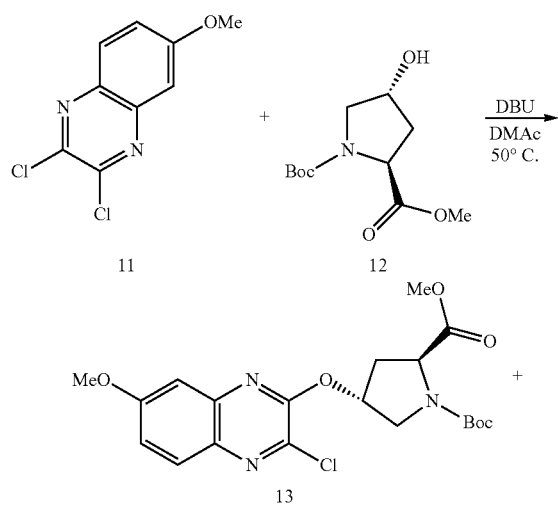

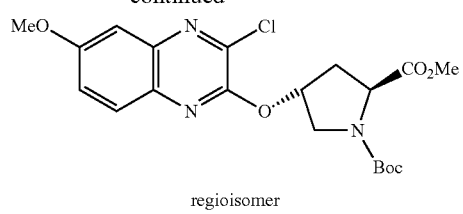

regioisomer

TABLE 3

| Materials | MW | Amount | Moles | Ratio |
|---|---|---|---|---|
| Compound 11 (93.5%) | 229.06 | 4.286 kg | 17.49 | 1 |
| N-Boc-4-trans-hydroxy-L-Proline methyl ester (98%) | 245.27 | 4.82 kg | 19.24 | 1.1 |
| DBU (98%) | 152.24 | 4.08 kg | 26.2 | 1.5 |
| DMAc | | 20 | | 5 V |
| DMSO/water (1:1) | | 22 L | | |
| 2.5N HCl | | 10 L | | |
| MTBE | | 68 L | | |
| Heptane | | | | |
| 16% NaCl | | 11 L | | |

To a 100 L cylinder reactor, equipped with an overhead stirrer, thermocouple, and nitrogen inlet, was charged 2,3-dichloro-6-methoxyquinoxaline Compound 11 (4.286 kg, 93.5 wt %), N-Boc-4-trans-hydroxy-L-Proline methyl ester Compound 12 (4.82 kg), and DMAc (20 L). The resulting reaction mixture was charged DBU (4.08 kg, or 4.04 L). The mixture was stirred at 50° C. for 20-30 h to afford products Compound 13 and a regioisomer (>98 LCAP % conversion). The reaction mixture was cooled to room temperature. Water (20 L) and MTBE (34 L) were added. After phase separation, the aqueous layer was back to extract with MTBE (34 L). The combined organic layers were washed with DMSO/water (1:1, 2×11 L), 2.5 N HCl (1×10 L), water (2×14 L) and 16% NaCl (11 L). Assay product Compound 12 in MTBE layer was about 6.72 kg (88%)

The reaction mixture was concentrated and azotroped by MTBE until the KF of the solution was <300 ppm, and adjusted to a total volume (18 L). The solution was seeded, and stirred at room temperature for 5 hours. Heptane (21.5 L) was slowly added over 2 hours. The resulting slurry was stirred at room temperature overnight, and at 5-10° C. for 2 hours. The crystalline solid was collected by filtration, washed with cold heptane/MTBE (3:1, 16 L), heptane (10 L), and dried under vacuum with nitrogen sweep to afford desired product Compound 13 (5.68 kg, 96.7 A %, 95.5 wt %, 71% isolated yield after correction), m.p. 98.5-99° C.

HPLC Conditions: Zorbax Eclipse Plus C18 50×4.6 mm, 1.8 um, 1.5 mL/min, 230 nm, 25° C., Eluents: Water 0.1% H$_3$PO$_4$ (A), Acetonitrile (B). 90% A 0 min, 5% A 5 min, 5% A 6 min.

Retention time for Compound 11: 4.486 min.

Retention time for Compound 12: 2.422 min.

Retention time for Compound 13: 4.990 min.

Retention time for regioisomer: 4.927 min.

Example 3

Macrolactam Production

Preparation of (S)-2-((((1R,2R)-2-(5-(3-(((3R,5S)-1-(tert-butoxycarbonyl)-5-(methoxycarbonyl)pyrrolidin-3-yl)oxy)-6-methoxyquinoxalin-2-yl)pent-4-yn-1-yl)cyclopropoxy)carbonyl)amino)-3,3-dimethylbutanoic acid (Compound 14)

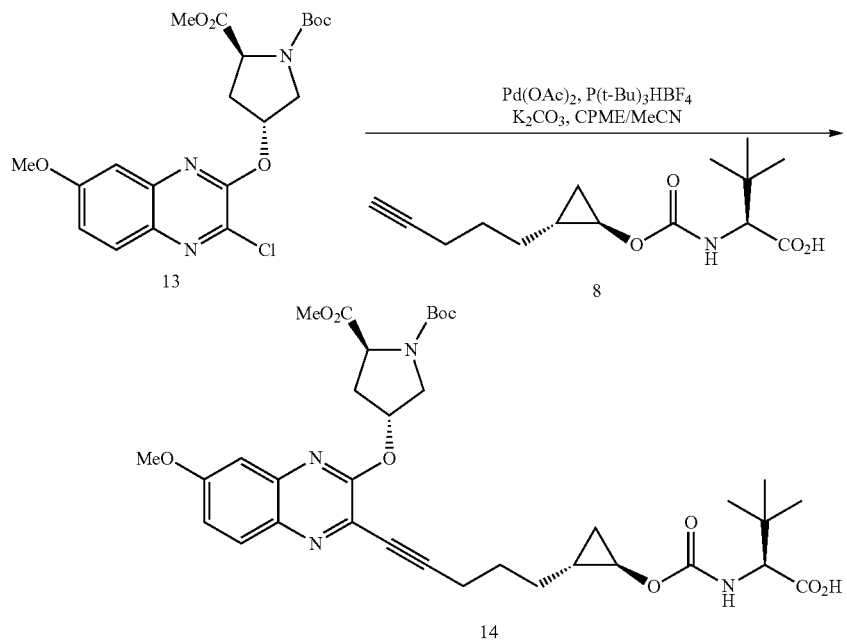

TABLE 4

| Materials | MW | Amount | mMole | Equiv |
|---|---|---|---|---|
| Chloride 13 | 437.87 | 6.00 g | 13.15 | 1.00 |
| Acetylene 8 | 281.35 | 5.42 g | 15.79 | 1.20 |
| Pd(OAc)$_2$ | 224.51 | 0.089 g | 0.395 | 0.03 |
| P(t-Bu)$_3$HBF$_4$ | 290.13 | 0.229 g | 0.789 | 0.06 |
| K$_2$CO$_3$ | 138.21 | 4.55 g | 32.9 | 2.50 |
| MeCN | | 16 L | | |
| 1M H$_3$PO$_4$ | 98.00 | 32.9 mL | 65.8 | 5.00 |

The above solution containing 5.42 g of acetylene Compound 8 (82 Wt % solution in MTBE) was solvent switched to a final volume of ~32 mL of CPME. To the resulting solution was added as a solid 6.00 g (96 wt %) of Compound 13 and the sides of the reaction flask. The slurry was warmed to an internal temperature of ~28-32° C. while sparging with N$_2$ and aged for 45 min to give a homogeneous solution.

In a separate 250 mL round bottom flask equipped with a mechanical stirrer, thermocouple, nitrogen inlet inserted in the flask, and reflux condenser was added sequentially as solids 89 mg of Pd(OAc)$_2$, 229 mg of P(t-Bu)$_3$HBF$_4$, and 4.55 g of K$_2$CO$_3$. The solids were diluted with 18 mL of MeCN and the slurry was sparged with N$_2$ for 35 min at room temperature. To the slurry was transferred via vacuum the above solution containing the acetylene and chloride starting materials and the final reaction mixture was sparged with N$_2$ an additional 15 min. The reaction mixture was heated to an internal temperature of 80-85° C. and aged at this temperature for 2.0 hours. HPLC analysis at this point confirmed complete consumption of Compound 13 (conversion >99%). The reaction mixture was cooled in an ice bath to bring the internal temperature to ~25-30° C.

In a separate 500 mL cylindrical extractor was placed 32.9 mL of a 1 M solution of H$_3$PO$_4$. To the solution was added 100 mL of IPAc. To the biphasic mixture was transferred the above reaction mixture slowly over 30 min.

The pH of the aqueous layer was confirmed to be ~1 at this point. The layers were well mixed for 15 min and allowed to separate. The bottom aqueous layer was drained and discarded. The organic layer was washed with 100 mL of water and then with 100 mL of brine. HPLC of the organic layer gave 8.40 g (93.5%) of Compound 14.

An analytical sample was obtained by silica gel chromatography and as a colorless foam: $^1$H NMR (CDCl$_3$, 400 MHz) δ 0.57 (q, 1H, J=6.3 Hz), 0.88 (m, 1H), 1.02 (s, 9H), 1.03 (m, 1H), 1.27 (m, 1H), 1.45 (br s, 11 H), 1.80 (m, 2H), 2.45 (m, 1H), 2.58-2.62 (m, 3H), 3.69-4.01 (m, 9H), 4.12 (m, 1H), 4.48 and 4.51 (t, due to rotamers, 1H, J=7.8 Hz), 5.30 (br m, 1H), 5.71 (br m, 1H), 7.10 (s, 1H), 7.29 (d, 1H, J=9.1 Hz), 7.84 (m, 1H, J=9.1 Hz); $^{13}$C NMR (CDCl$_3$, 100 MHz) δ 11.9, 17.6, 18.3, 19.2, 26.2, 26.8, 27.2, 27.4, 28.0, 28.6, 29.1, 29.7, 30.2, 34.4, 35.6, 36.5, 52.0, 54.8, 55.1, 55.4, 55.6, 55.8, 57.8, 58.2, 62.1, 73.8, 74.1, 80.7, 97.4, 105.6, 106.1, 119.3, 119.8, 129.1, 129.6, 129.8, 134.3, 140.7, 153.9, 154.5, 156.4, 156.8, 161.4, 173.3, 174.4.

HPLC Conditions: Zorbax Eclipse Plus C18 50×4.6 mm, 1.8 um, 1.5 mL/min, 210 nm, 25° C., Eluents: Water 0.1% H$_3$PO$_4$ (A); MeCN (B). 90% A to 50% A 2 min, 27% A 5 min, 21% A 5.2 min, 5% A 6 min, 90% A 6.1 min

| | |
|---|---|
| Compound 13 | 5.5 min |
| Compound 14 | 5.7 min |

Preparation of (S)-2-((((1R,2R)-2-(5-(3-(((3R,5S)-1-(tert-butoxycarbonyl)-5-(methoxycarbonyl)pyrrolidin-3-yl)oxy)-6-methoxyquinoxalin-2-yl)pentyl)cyclopropoxy)carbonyl)amino)-3,3-dimethylbutanoic acid (Compound 15)

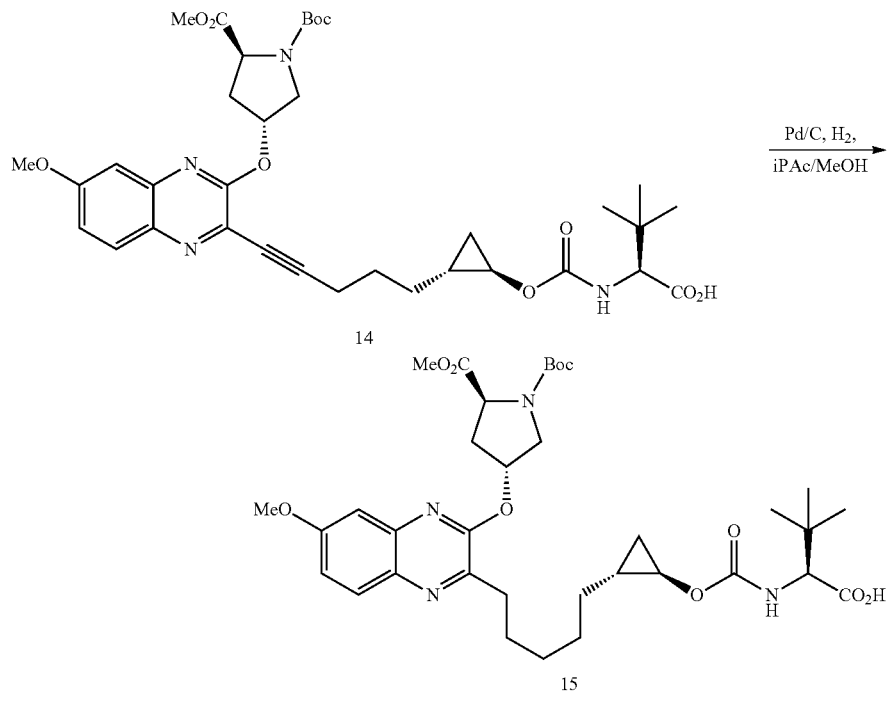

TABLE 5

| Materials | MW | Amount | mMole | Equiv |
|---|---|---|---|---|
| Acetylene SM 14 | 682.76 | 8.1 g | 11.86 | 1.00 |
| 5% Pd/C | 106.42 | 505 mg | 0.237 | 0.02 |

To the crude acetylene 8.10 g in ~20 L of 2:1 IPAc/MeOH was added 505 mg of 5% Pd/C. The reaction was placed under vacuum and purged with hydrogen (3×) and hydrogenated under balloon pressure of $H_2$ for 2 hours at which point the reaction was complete by HPLC.

The reaction mixture was filtered through Solka floc eluting with IPAc. The filtrate was then concentrated under reduced pressure in a 100 mL round bottom flask equipped with a thermocouple, mechanical stirrer, and batch concentrator. The solvent was switched to MeCN and a final volume of ~50 mL. Final assay of the combined batches was 7.25 g (89%) of the product Compound 15. The crude product was used without further purification in the next step.

An analytical sample was obtained by silica gel chromatography and as a colorless foam: $^1$H NMR (CDCl$_3$, 400 MHz) δ 0.50 (q, 1H, J=6.3 Hz), 1.04 (br s, 11 H), 1.20 (br s, 3H), 1.45 (br s, 13 H), 1.72 (m, 2H), 2.40 (m, 1H), 2.63 (m, 1H), 2.93 9m, 2H), 3.68-3.94 (m, 9H), 4.15 (br m, 1H), 4.46 and 4.60 (t, due to rotamers, 1H, J=7.8 Hz), 5.27 (br m, 1H), 5.78 (br m, 1H), 7.18 (m, 1H), 7.20 (m, 1H), 7.85 (m, 1H); $^{13}$C NMR (CDCl$_3$, 100 MHz) δ 11.9, 18.5, 26.6, 27.0, 28.1, 28.3, 28.4, 29.1, 30.9, 32.9, 34.1, 35.7, 36.6, 49.4, 52.1, 52.2, 52.4, 55.1, 55.7, 57.7, 58.2, 62.3, 73.5, 74.1, 80.7, 106.0, 118.8, 128.5, 133.7, 141.1, 148.2, 153.9, 154.5, 155.3, 157.1, 160.4, 173.2, 173.3, 174.4.

HPLC Conditions: Zorbax Eclipse Plus C18 50×4.6 mm, 1.8 um, 1.5 mL/min, 210 nm, 25° C., Eluents: Water 0.1% $H_3PO_4$ (A); MeCN (B). 90% A to 50% A 2 min, 27% A 5 min, 21% A 5.2 min, 5% A 6 min, 90% A 6.1 min

| Compound 14 | 5.7 min |
|---|---|
| Compound 15 | 6.2 min |

Preparation of Macrolactam Methyl Ester (Compound 17)

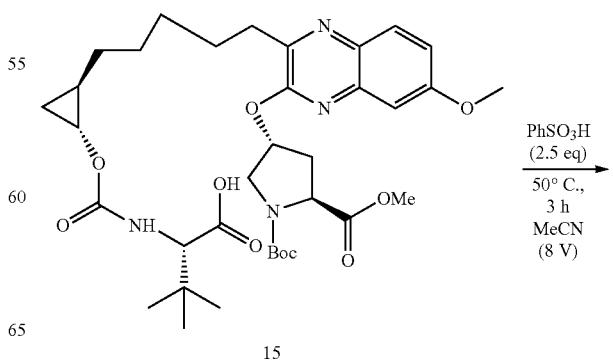

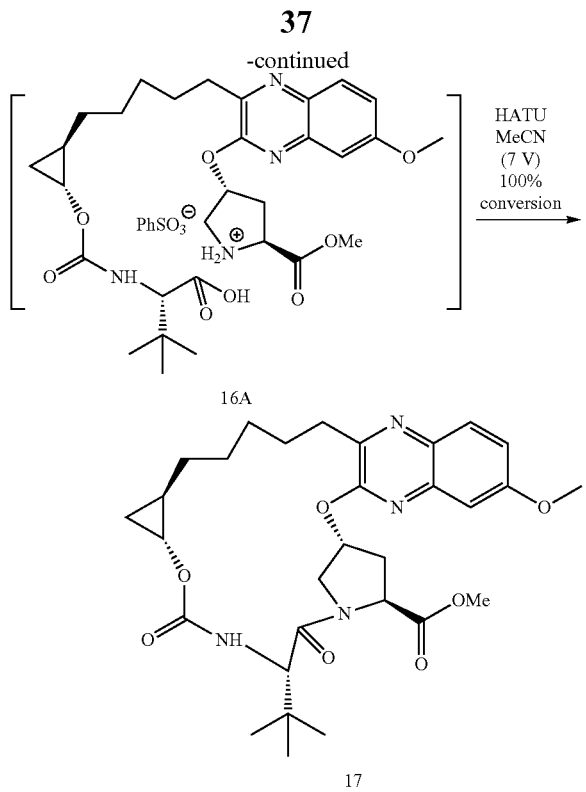

16A

17

TABLE 7

| Materials | MW | Amount | Moles | Ratio |
|---|---|---|---|---|
| Compound 15 | 686.79 | 3.510 kg | 5.111 | 1 |
| PhSO₃H (98%) | 158.18 | 2.062 kg | 12.78 | 2.5 |
| MeCN | | 28 L | | 8 V |
| Hunig's Base (98%) d = 0.742 | 129.24 | 3.064 kg (4.09 L) | 23.00 | 4.5 |
| MeCN | | 24.6 L | | 7 V |
| HATU (97%) | 380.23 | 2.70 kg | 6.900 | 1.35 |
| Cold MeCN | | 6 L | | |
| Heptane | | 8 L | | |

To a 50 L cylinder reactor, equipped with an overhead stirrer, thermocouple, and nitrogen inlet, was charged Compound 15 (poly jug #1: 9.9 kg×19.1 wt %=1.89 kg; and poly jug #4: 9.0 kg×18.0 wt %=1.62 kg) in acetonitrile solution. Benzenesulfonic acid (2.062 kg) in acetonitrile (10 L) was added over 10 min. The resulting solution was stirred at 50° C. for 3-5 hours (>99.5 A % conversion) to afford intermediate 16A.

The reaction mixture was cooled to room temperature. Hunig's base (4.09 L) was slowly added at <30° C. The resulting solution was stirred at room temperature for 0.5 hour. At this point, the pH of the solution should be about 8-9.

To a 100 L round bottomed flask, equipped with an overhead stirrer, thermocouple, and nitrogen inlet, was charged HATU [O-(7-azabenzotriazol-1-yl)-N,N,N',N'-tetramethyluronium hexafluorophoshate] (2.70 kg) and acetonitrile (24.6 L) at room temperature. To the resulting solution was slowly added intermediate Compound 16A in Hunig's base/acetonitrile solution over 8 hours with a rate about 80 mL/min. After the addition, product Compound 17 precipitated out. The resulting slurry was stirred at room temperature to allow the reaction to complete (100 A % conversion).

The slurry was concentrated to a total volume (18 L), and then aged at 5-10° C. for 3 hours. The crystalline solid was collected by filtration, washed with cold acetonitrile (6 L), and heptane (8 L), dried under vacuum with nitrogen sweep to afford desired product Compound 17 (1.90 kg, 65% isolated yield, 97.3 A % purity, assay 100 wt %), m.p. 230.3-231.3° C. The X-ray data of Compound 17 is shown in FIG. 1.

HPLC Conditions: Zorbax Eclipse Plus C18 50×4.6 mm, 1.8 um, 1.5 mL/min, 230 nm, 25° C., Eluents: Water 0.1% H₃PO₄ (A), Acetonitrile (B). 90% A 0 min, 5% A 5 min, 5% A 6 min.

Retention time for Compound 15: 5.270 min.
Retention time for Compound 16A: 3.273 min.
Retention time for Compound 17: 5.423 min.

Saponification (Compound 18)

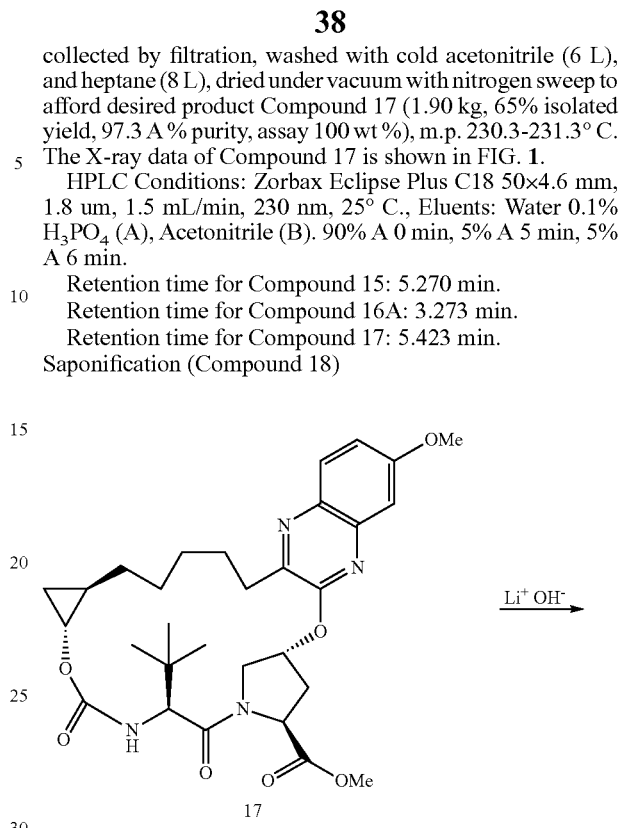

17

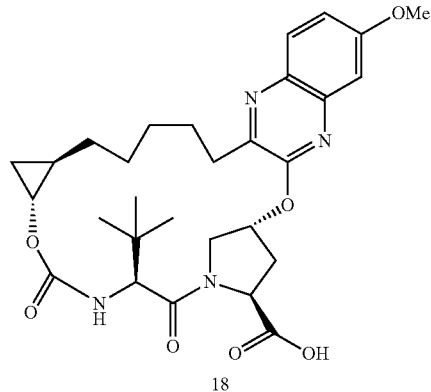

18

TABLE 8

| Material | MW | Equiv | Mass (kg) | Mol | Vol (L) |
|---|---|---|---|---|---|
| Methyl Ester (17) 97.5% | 568.66 | 1.0 | | 3.5 | 6.0 |
| LiOH | 2N | 5.0 | | 30.0 | 15.0 |
| HCl | 12N | 5.0 | | 30.0 | 2.5 |
| THF | | | | | 17.5 |
| Ethyl Acetate | | | | | 53 |
| Brine 10% | | | | | 18 |
| Hexanes | | | | | 38.5 |
| Hexanes/EtOAc 4:1 | | | | | 8.75 |

To a 100 L Buchi reactor vessel fitted with a N₂ inlet and a temperature probe, was charged THF (17.5 L), methyl ester (Compound 17), and LiOH solution (15.0 L). The mixture was heated to 40° C. and aged for 1 hour. After cooling to 14° C., concentrated HCl was added till a pH of 1.9 at 20° C. was obtained. To the mixture was added 53 L ethyl acetate. The layers were cut and the organic layer was washed once with 81 L 10% brine solution. The organic solution was stored overnight in poly jugs.

The ethyl acetate/THF solution was concentrated to 4 volumes (14 L) and then flushed with 18 L ethyl acetate keeping the volume constant at 14 L. To the slurry was added 38.5 L hexanes over 4 hours. The slurry was aged overnight at ambient temperature.

Figure 2:
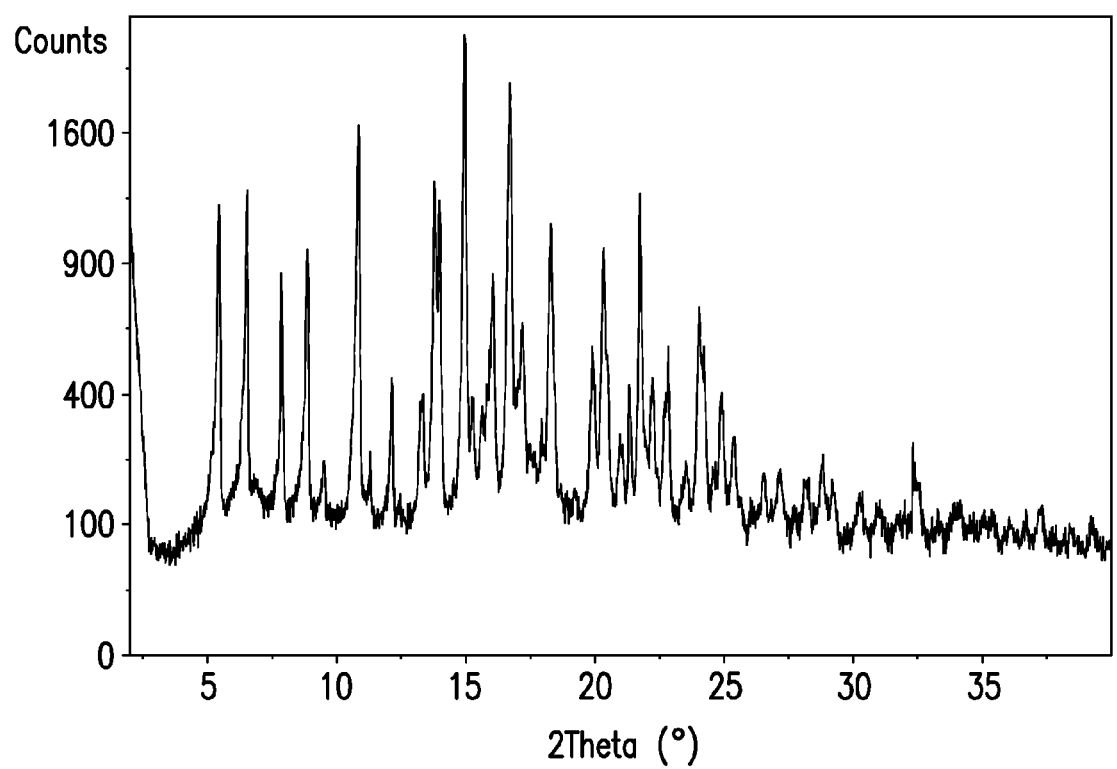
FIG. 2 illustrates an X-ray diffraction pattern of a crystalline Compound 18.

The slurry was filtered, washed with 8.75 L of 4:1 hexanes: EtOAc, and dried under vacuum with a $N_2$ sweep at ambient temperature for 60 hours to give product 18 (3.36 kg, 98% isolated yield, 98.7 LCAP %), m.p. 248.5-249.5° C. The X-ray data of Compound 18 is shown in FIG. 2.

| Analytical Data | |
|---|---|
| Relative RT | Area % |
| 0.75 | 1.11 |
| 1.05 | 0.25 |
| 1.12 | 0.61 |
| 1.18 | 0.14 |
| total imp | 2.11 |
| Acid | 97.89 |

HPLC Conditions:
Column: Zorbax Eclipse Plus C18 50×4.6 nm 1.8 um
Gradient: A=ACN, C=Buffer 0.1% $H_3PO_4$
10% A to 95% A over 6 min to 10% A over 0.1 min. hold till 8 min.
Flow=1.5 mL/min
Temp 25° C.
Wavelength=210 nm
Retention Times: Methyl ester 34=5.421 min, Carboxylic acid 17=4.827 min Boc De-Protection of Side Chain (Compound 19)

TABLE 9

| Material | MW | Equiv | Mass (kg) | Mol |
|---|---|---|---|---|
| Boc side chain | 330.40 | 1 | 2.261 | 6.84 |
| TsOH monohydrate 98.5% | 190.22 | 1.8 | 2.34 | 12.12 |
| Ethyl Acetate | | | | 33.6 |

The Boc-sulfonamide was charged in a 75 L 4-neck round bottomed flask fitted with overhead stirrer, temperature probe, and $N_2$ inlet. Ethyl acetate (22.6 L) was added followed by the TsOH. The mixture was aged at ambient temperature for 23.5 hours The mixture is homogeneous at the start, but forms precipitates during the overnight age giving a free flowing white slurry.

The solids (Compound 19) were filtered, washed with 11 L ethyl acetate and dried under vacuum with a $N_2$ sweep at ambient temperature for 48 hours.

$^1$H NMR: Solids after drying=0.5% w/w ethyl acetate.

Net Wt=2.611 kg=94.5% IY

Purity=99.8 LCAP

| Analytical Data | |
|---|---|
| Relative RT | Area % |
| 0.41 | 0.10 |
| 1.31 | 0.25 |
| total imp | 0.35 |
| side chain | 99.65 |

HPLC Conditions:

Column: Zorbax Eclipse Plus C18 50×4.6 nm 1.8 um

Gradient: A=ACN, B=Buffer 0.1% $HClO_4$

5% A to 95% A over 6 min to 10% A over 0.1 min. hold till 8 min.

Flow=0.5 mL/min

Temp 25° C.

Wavelength=210 nm

Retention Times: Boc-protected side chain=3.455 min; De-Boc Compound 19=0.646 min Preparation of Compound A Free Acid

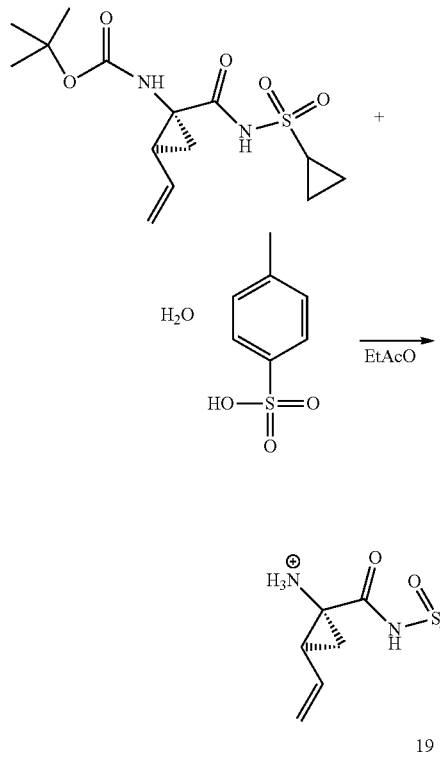

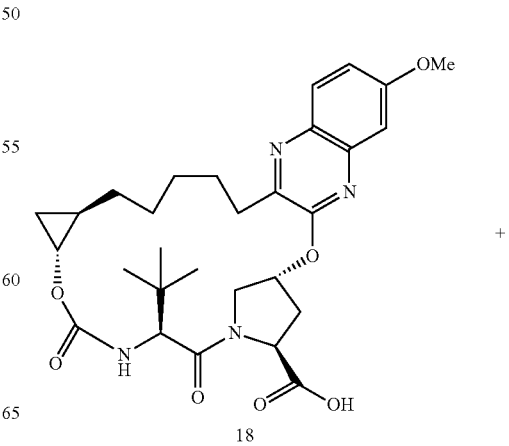

-continued

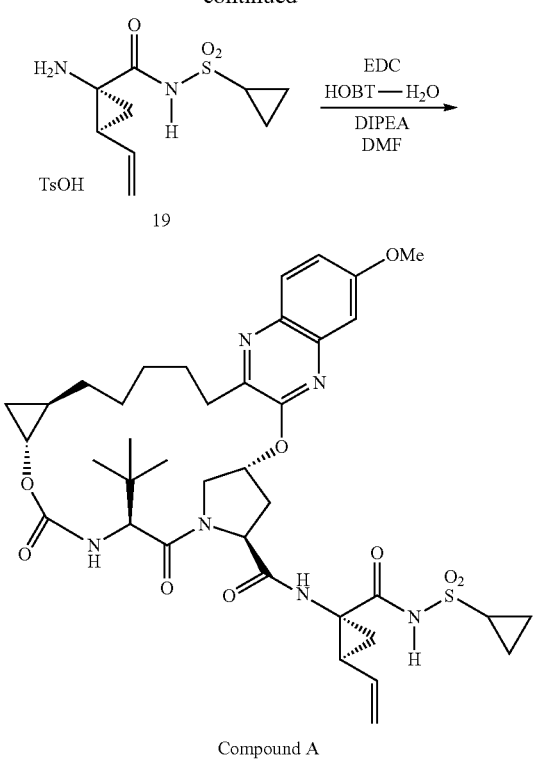

Compound A

TABLE 10

| Materials | MW | Amount | Moles | Equiv |
|---|---|---|---|---|
| carboxylic acid 18 | 554.63 | 2.70 kg | 4.87 | 1.00 |
| cyclopropyl amine 19 | 402.49 | 2.52 kg | 5.84 | 1.20 |
| HOBt—H$_2$O | 153.14 | 1.79 kg | 11.68 | 2.40 |
| DIPEA | 129.24 | 2.04 L | 11.68 | 2.40 |
| EDC | 191.70 | 1.12 kg | 5.84 | 1.20 |
| DMF | | 15 L | | |
| MeCN | | 30 L | | |
| 1M HCl | | 10.7 L | 10.70 | 2.2 |
| Water | | 33.5 L | | |

In a 50 L jacketed cylindrical vessel equipped with a mechanical stirrer, thermocouple and nitrogen inlet containing 5 L DMF was added the carboxylic acid (Compound 18), the cyclopropyl amine (Compound 19) and HOBt-H$_2$O with stirring. The walls of the flask were rinsed with 10 L DMF and to the resulting mixture was added the DIPEA while the flask was cooled at 10° C. The resulting brown slurry was stirred for 30 min.

To the resulting solution was added portion wise the EDC. The resulting solution was then stirred at 18° C. for 18 hours. The brown solution was then transferred to a 100 L RBF containing 10 L MeCN and equipped with a mechanical stirrer, thermocouple, dropping funnel and nitrogen inlet. The 50 L jacketed cylindrical vessel was flushed with 5 L MeCN. To this brown solution was slowly added the 1M HCl from the dropping funnel while cooling in an ice bath, maintaining an internal temperature below 22° C.

To the resulting orange solution was then added slowly from the dropping funnel 20 L of water. The resulting slurry was stirred for 3 hours at ambient temperature and then filtered.

The wet cake was washed with 30 L of 1:1 MeCN:H$_2$O and then dried under N$_2$/vacuum sweep to give 3.66 kg of Compound A (94 wt %, 95.2 LCAP, 92% yield).

HPLC Conditions: Zorbax Eclipse Plus C18 50×4.6 mm, 1.8 um, A=0.1% phosphoric acid, C=Acetonitrile: 10% to 95% C, 5 min; 95% C, 6 min; 10% C, 6.1 min; 2 min post, 1.5 mL/min, 230 nm, 25 C.

| Compound 18 | 4.85 min |
|---|---|
| Compound 19 | 0.79 min |
| Compound A | 5.41 min |

Example 4

Alternative Coupling Procedure for Producing Compound A

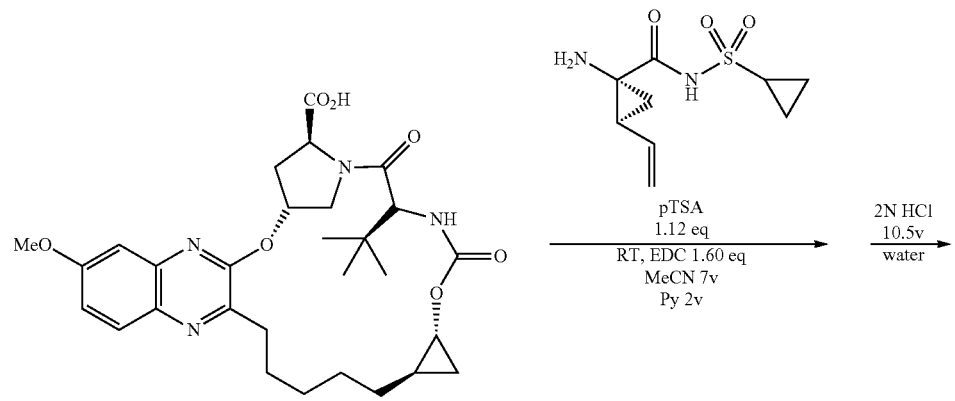

-continued

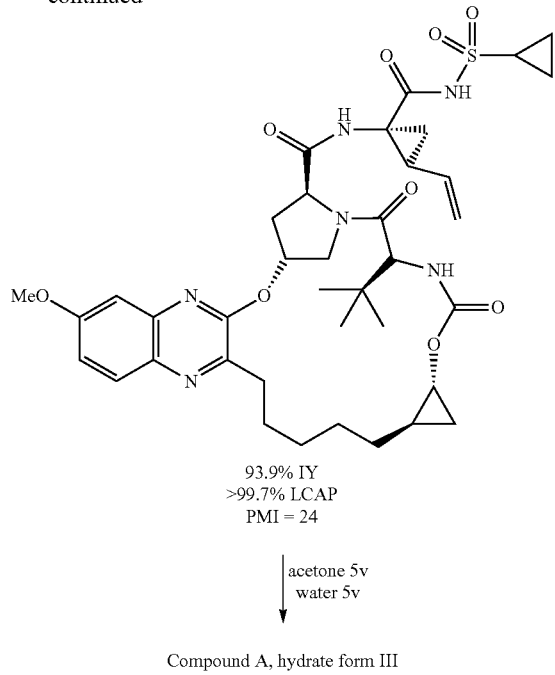

93.9% IY
>99.7% LCAP
PMI = 24

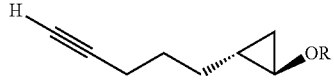

Compound A, hydrate form III

TABLE 12

| Materials | MW | Amount | Moles |
|---|---|---|---|
| Mac-acid Penultimate (18) | 554.6 | 1.06 kg | 1.91 (1.00 eq) |
| Amine-pTSA (19) | 402.5 | 0.86 kg | 2.14 (1.12 eq) |
| EDC-HCl | 191.70 | 0.59 kg | 3.06 (1.60 eq) |
| Pyridine | | 2.12 L | (13.7 eq) |
| MeCN | | 7.42 L | |
| HCl | 2N | 11.1 L | 22.2 (11.6 eq) |
| MeCN/water | | 8.0 L | |
| Water | | 6.0 L | |

To a 50 L round bottomed flask with overhead stirring was added Mac-acid 18 (1.06 kg crude, 1.00 eq), amine-pTSA (19, 862 g crude, 1.12q) and MeCN 7.42 L at 19° C. The slurry was cooled in a water bath, pyridine (2.12 L, 13.8 eq) was added, aged 15 minutes, and then added EDC (586 g, 1.60 eq) in one portion, aged 1.5 hours while it turned into a clear homogeneous solution.

The solution cooled in a water bath, then quenched with 2 N HCl (1.7 L), seeded (9.2 g), aged 15 minutes, and the rest of the aqueous HCl was added over 2.5 hours. A yellow slurry was formed. The slurry was aged overnight at RT, filtered, washed with MeCN/water (1:1v/v) 8 L, to obtain Compound A (Hydrate II).

Compound A was dissolved in acetone 4 L at RT, filtered and transferred to a 12 L RBF with overhead stirring, rinsed with extra acetone 1 L, heated to 50° C., water 0.9 L was added, seeded 10 g, aged 15 minutes, then added water 0.8 L over 2.5 hours, extra water 3.3v over 2.5 hours was added, stopped heating, cooled to RT, aged at RT overnight, filtered, washed with water/acetone (1:1v/v) 4 L, and dried in air under vacuum. Compound A Hydrate III, 670 g, was obtained as an off-white solid.

None of the references described throughout the present application are admitted to be prior art to the claimed invention.

What is claimed is:
1. A compound selected from the group consisting of:

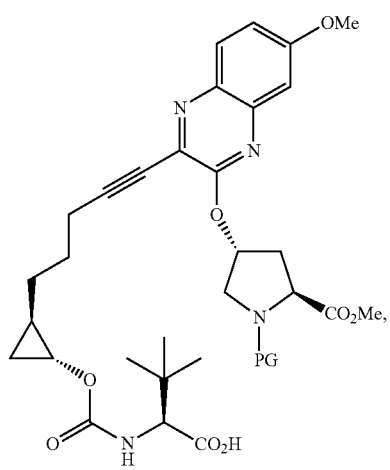

wherein R is either H, acetyl, or C(O)NHCH(X)COOH, and X is a $C_2$-$C_6$ alkyl, or a $C_3$-$C_8$ cycloalkyl,

14

-continued

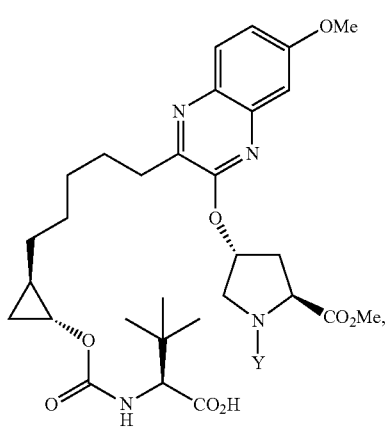

and salts thereof, wherein Y is a protecting group or H and wherein PG is a protecting group.

2. The compound of claim 1, wherein said compound is

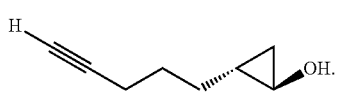

3. A method of making Compound 6, comprising the step of reacting

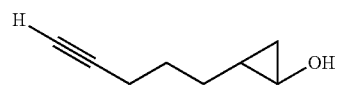

(Compound 5) with an acetylating agent to produce

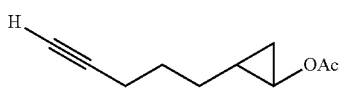 [SMILES: C#CCCCC1CC1OC(C)=O]

(Compound 6).

4. The method of claim 3, wherein Compound 5 is produced by reacting

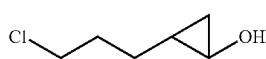

(Compound 4) with a metal acetylide to produce Compound 5.

5. The method of claim 4, wherein Compound 4 is produced by oxidizing

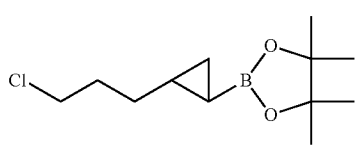 [SMILES: CC1(C)OB(C2CC2CCCCl)OC1(C)C]

(Compound 3).

6. The method of claim 5, wherein Compound 3 is produced by reacting

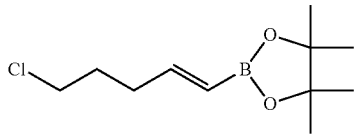

(Compound 2) with an alkyl zinc reagent, an acid and a dihalomethane in a halogenated solvent at a temperature between 0° C. and 40° C., followed by addition of an acidic aqueous solution and separation of the organic layer to obtain Compound 3.

7. A method of making a compound of Formula I

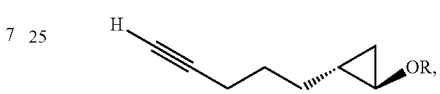

wherein R is C(O)NHCH(X)COOH, X is a $C_2$-$C_6$ alkyl, or a $C_3$-$C_8$ cycloalkyl; or a salt thereof; comprising the step of reacting

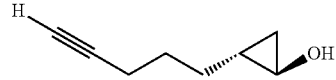

(Compound 7) with

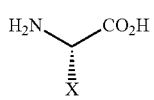

to produce Compound 8.

8. A method of producing Compound 13, comprising the step of reacting Compound 11 with Compound 12 to produce Compound 13:

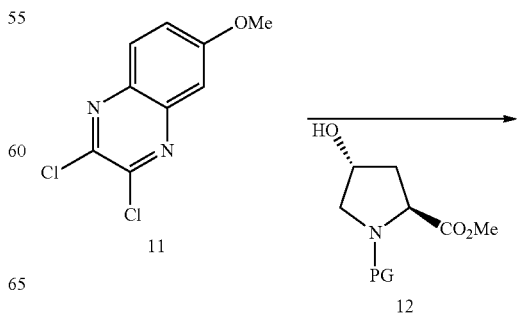

-continued

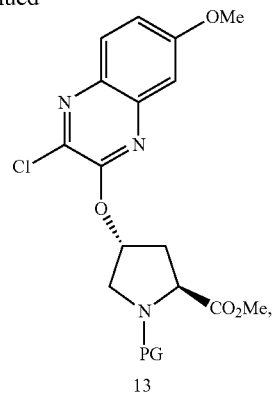

13 wherein PG is a protecting group.

9. The method of claim 8, comprising steps of reacting Compound 9 with HCl and oxalic acid to produce Compound 10 and further reacting Compound 10 with POCl$_3$ to produce Compound 11 or salts thereof:

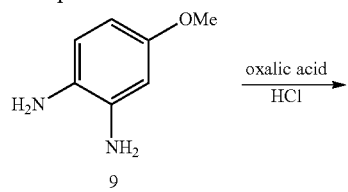

9

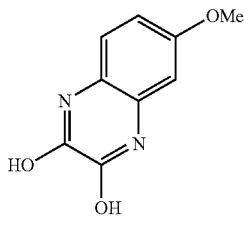

10

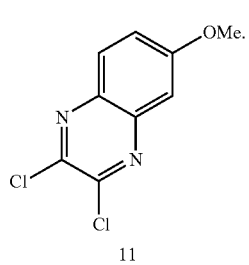

11

10. A method of producing Compound 14 comprising the step of reacting Compound 13 with Compound 8 to produce Compound 14 or salts thereof:

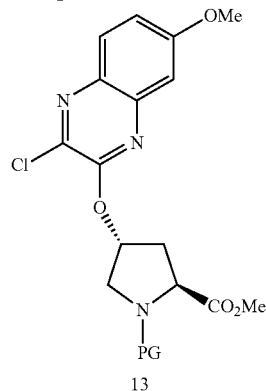

13

-continued

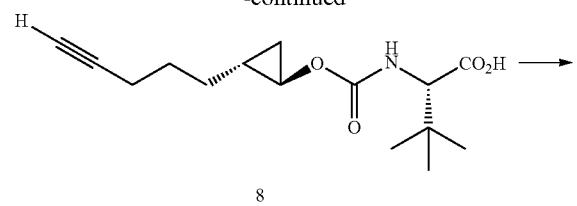

8

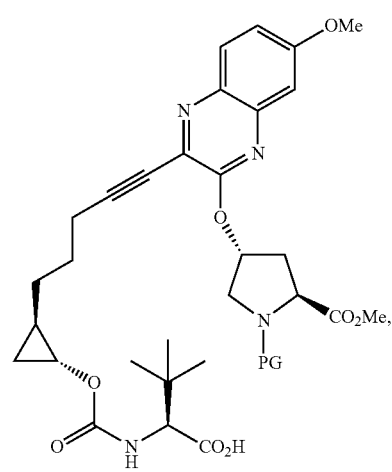

14 wherein PG is a protecting group.

11. The method of claim 10, wherein the reaction uses tri tert-butylphosphine tetra fluoroborate salt in a solvent, and Compound 8 is provided as either a dibenzylamine salt or a t-butylamine salt.

12. The method of claim 10, further comprising the steps of:

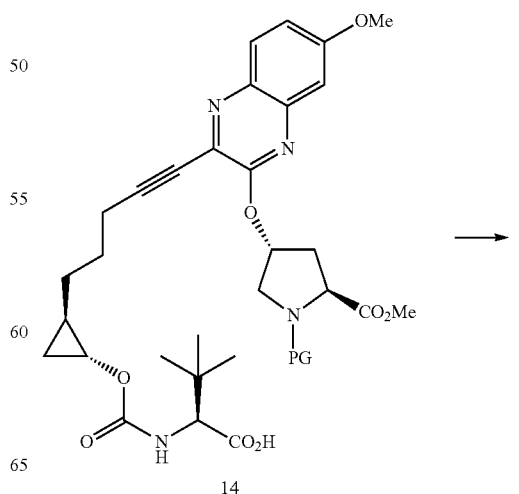

14

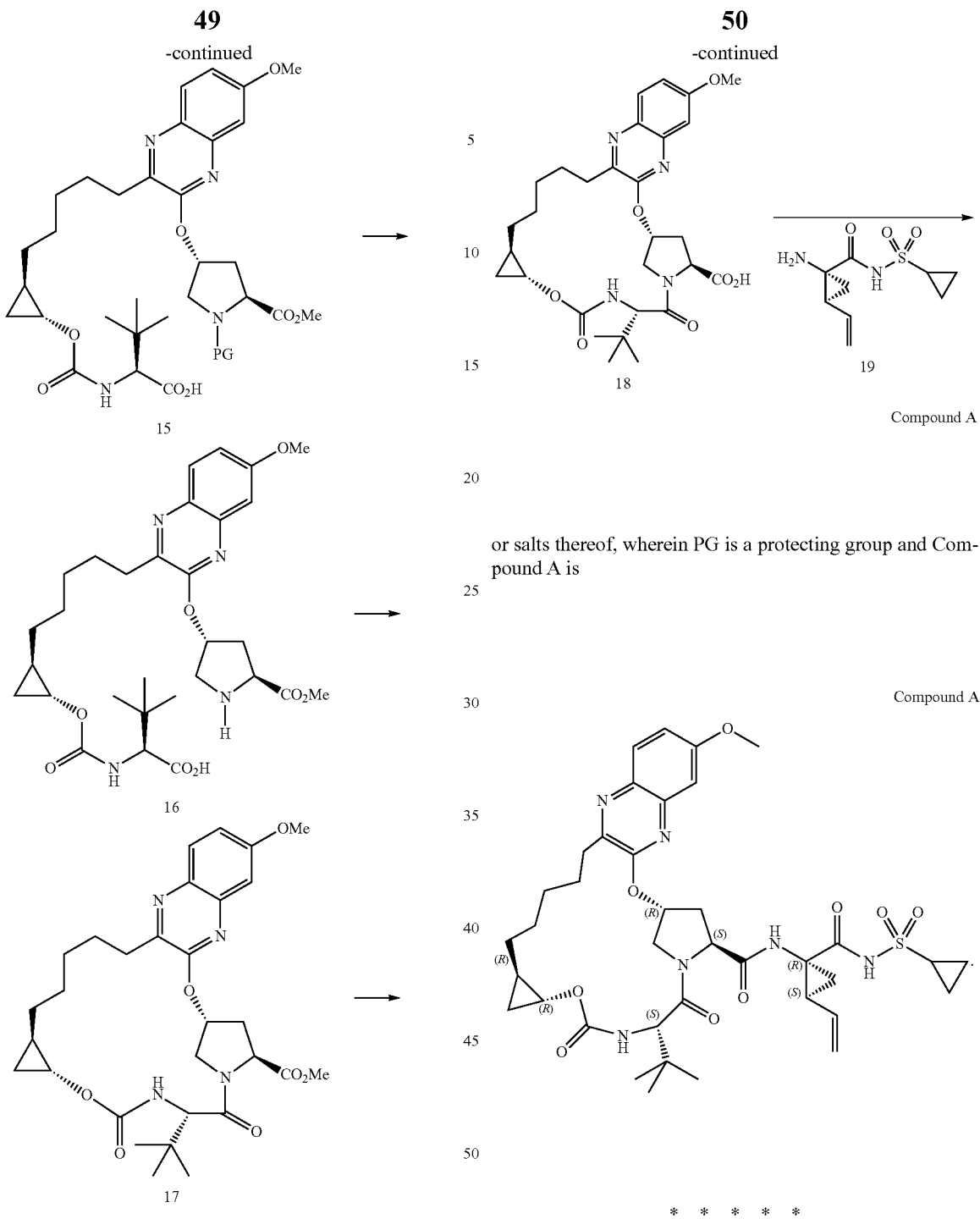
or salts thereof, wherein PG is a protecting group and Compound A is
Compound A
* * * * *